(12) United States Patent
Su et al.

(10) Patent No.: US 7,989,651 B2
(45) Date of Patent: Aug. 2, 2011

(54) EPOXYSILANES, PROCESSES FOR THEIR MANUFACTURE AND CURABLE COMPOSITIONS CONTAINING SAME

(75) Inventors: Shiu-Chin H. Su, Croton-on-Hudson, NY (US); Kendall L. Guyer, Carmel, NY (US); Eric R. Pohl, Mount Kisco, NY (US); Alexander S. Borovik, White Plains, NY (US)

(73) Assignee: Momentive Performance Materials Inc., Albany, NY (US)

( * ) Notice: Subject to any disclaimer, the term of this patent is extended or adjusted under 35 U.S.C. 154(b) by 1090 days.

(21) Appl. No.: 11/716,334

(22) Filed: Mar. 9, 2007

(65) Prior Publication Data

US 2008/0221238 A1 Sep. 11, 2008

(51) Int. Cl.
*C07F 7/04* (2006.01)
(52) U.S. Cl. ........................................ 556/436; 556/413
(58) Field of Classification Search ........................ None
See application file for complete search history.

(56) References Cited

U.S. PATENT DOCUMENTS

| | | | |
|---|---|---|---|
| 3,455,877 A | 7/1969 | Plueddemann | |
| 3,632,557 A | 1/1972 | Brode | |
| 3,927,042 A * | 12/1975 | Golitz et al. | 549/215 |
| 3,979,344 A | 9/1976 | Bryant et al. | |
| 4,020,043 A | 4/1977 | Siefken | |
| 4,067,844 A | 1/1978 | Barron et al. | |
| 4,222,925 A | 9/1980 | Bryant et al. | |
| 4,328,346 A | 5/1982 | Chung et al. | |
| 4,345,053 A | 8/1982 | Rizk et al. | |
| 4,374,237 A | 2/1983 | Berger et al. | |
| 4,625,012 A | 11/1986 | Rizk et al. | |
| 4,645,816 A | 2/1987 | Pohl et al. | |
| 4,705,841 A | 11/1987 | Tosh et al. | |
| 5,550,272 A | 8/1996 | Lewis et al. | |
| 5,587,502 A | 12/1996 | Moren et al. | |
| 5,616,762 A | 4/1997 | Kropfgans et al. | |
| 5,905,150 A | 5/1999 | Simonian et al. | |
| 6,001,907 A | 12/1999 | Huang | |
| 6,197,912 B1 | 3/2001 | Huang et al. | |
| 6,361,868 B1 | 3/2002 | Bier et al. | |
| 6,391,999 B1 | 5/2002 | Crivello | |
| 6,849,337 B2 | 2/2005 | Ohrbom et al. | |

FOREIGN PATENT DOCUMENTS

| | | |
|---|---|---|
| DE | 20 37 617 A1 * | 1/1972 |
| DE | 40 08 343 A * | 9/1990 |
| EP | 1 403 953 A * | 3/2004 |
| JP | 03 254868 A * | 3/2004 |
| WO | WO 95/31511 A * | 11/1995 |
| WO | WO01/98403 A2 | 5/2001 |

OTHER PUBLICATIONS

Peter A. Edwards, Grant Striemer, and Dean C. Webster,*Novel Polyurethane Coating Technology Through Glycidyl Carbamate Chemistry*, Jul. 2005, JCT Research, vol. 2, No. 7, pp. 517-527.

* cited by examiner

*Primary Examiner* — Daniel Sullivan
*Assistant Examiner* — Yevegeny Valenrod
(74) *Attorney, Agent, or Firm* — Dominick G. Vicari; Joseph S. Ostroff

(57) ABSTRACT

Epoxysilanes are provided which contain at least one epoxy group, at least one hydrolyzable silyl group and one or more linkages containing a carbonyl group bonded to heteroatoms selected from the group consisting of oxygen, sulfur and nitrogen with at least one such heteroatom being nitrogen, there being no such linkage in which both an epoxy group and hydrolyzable silyl group are directly or indirectly bonded to the same nitrogen heteroatom in the linkage.

38 Claims, No Drawings

EPOXYSILANES, PROCESSES FOR THEIR MANUFACTURE AND CURABLE COMPOSITIONS CONTAINING SAME

BACKGROUND OF THE INVENTION

This invention relates to epoxysilanes, their manufacture, curable compositions containing epoxysilanes and applications of epoxysilanes.

Known epoxysilanes such as 3-glycidoxypropyltrimethoxysilane find use, inter alia, as adhesion promoters, coatings and crosslinkers. Many of these and other uses of epoxysilanes would stand to benefit from higher adhesive strengths, better environmental resistance and more controllable cure times. Independently controlling the reactivity of the epoxy and hydrolyzable silyl groups and polarity of a curable epoxysilane are believed to be key to obtaining these desirable end-use characteristics. Known epoxysilane compounds often do not have the desired reactivity or adherence to substrates. Therefore, a need exists for epoxysilanes with controllable reactivity and better adhesion properties than the known epoxysilanes.

While numerous epoxysilane compounds are known, heretofore there appears to have been no epoxysilane possessing both epoxy and silyl functionalities and containing at least one carbonyl linkage bonded to heteroatoms selected from the group consisting of oxygen, sulfur, and nitrogen with at least one such heteroatom being nitrogen. It has now been discovered that providing an epoxysilane with at least one such carbonyl linkage results in improvement of one or more of its properties such as those aforementioned.

BRIEF SUMMARY OF THE INVENTION

In accordance with the present invention, epoxysilanes are provided which contain at least one epoxy group, at least one hydrolyzable silyl group and one or more linkages containing a carbonyl group bonded to heteroatoms selected from the group consisting of oxygen, sulfur and nitrogen with at least one such heteroatom being nitrogen, there being no such linkage in which both an epoxy group and a hydrolyzable silyl group are directly or indirectly bonded to the same nitrogen heteroatom in the linkage.

Further in accordance with the invention, a number of synthetic processes are provided for the manufacture of the expoxysilanes herein.

The presence of one or more of the aforesaid linkages in the epoxysilanes of the present invention is believed to control the reactivity of the epoxy and hydrolyzable silyl groups with attendant benefits for the application of the epoxysilanes, e.g., as adhesion promoters, coating intermediates and crosslinkers. When these linkages are in relatively close proximity to the epoxy and hydrolyzable silyl groups of the epoxysilane, they tend to increase the reactivity of these groups. Apart from this increased reactivity, the presence of one or more of the foregoing carbonyl group—heteroatom linkages greatly expands the range of structures for epoxysilanes allowing for considerable flexibility in the molecular design of these compounds and as a consequence, greater control over their functional properties for particular applications.

The term "epoxy" as used herein shall be understood to include compounds that contain at least one epoxy ring,

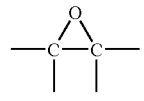

or episulfide ring,

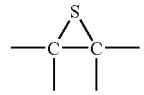

Thus, the term "epoxysilane" shall be understood to include compounds possessing at least one epoxy ring and/or episulfide ring, at least one hydrolyzable silyl group and one or more linkages containing a carbonyl group bonded to heteroatoms selected from the group consisting of oxygen, sulfur and nitrogen with at least one such heteroatom being nitrogen, there being no such linkage in which both an epoxy ring and/or episulfide ring and a hydrolyzable silyl group are directly or indirectly bonded to the same nitrogen heteroatom in the linkage. The foregoing linkages are inclusive of the structures

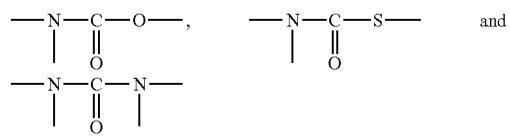

one or more of which can be present in an epoxysilane according to the invention.

As used herein in connection with the epoxysilanes of the present invention, the expression "an epoxy group and a hydrolyzable silyl group are directly or indirectly bonded to the same nitrogen heteroatom in the linkage" means that the hydrolyzable silyl group(s) and the epoxy group(s) are bonded through a hydrocarbyl group, optionally containing heteroatoms of oxygen, sulfur or nitrogen, to the different heteroatoms of the linkage and therefore that the hydrolyzable silyl group(s) and the epoxy group(s) are separated from each other by the carbonyl group of the linkage.

DETAILED DESCRIPTION OF THE INVENTION

The epoxysilanes of this invention possess at least one epoxy and/or episulfide group and at least one hydrolyzable silyl group joined together through a bridging group possessing one or more linkages containing a carbonyl group bonded to heteroatoms selected from the group consisting of oxygen, sulfur and nitrogen with at least one such heteroatom being nitrogen, there being no such linkage in which both an epoxy group and a hydrolyzable silyl group are directly or indirectly bonded to the same nitrogen heteroatom in the linkage.

The epoxy and episulfide functional groups are capable of reacting with a large variety of organofunctional groups such as nucleophiles, including the non-limiting examples of alkoxides, carboxylates, mercaptides, carbanions and the like; electrophiles, including the non-limiting examples of metal ions, anhydrides, acids, and the like; and free radicals, including the non-limiting examples of carbon radicals, oxy radicals, sulfuryl radicals, and the like. The broad range of the epoxy and episulfide reactivity allows these groups to participate in a large variety of curing chemistries, graphing chemistries and polymerization chemistries.

The hydrolyzable silyl groups react with moisture to generate silanols which condense with themselves to form siloxanes, react with surfaces oxides and surface hydroxyls to form silicon-oxygen-metal bonds or silicon-oxygen-non-metal bonds. The hydrolysis and condensation chemistries of the hydrolyzable silyl make these compounds suitable for crosslinking resins and polymers or to bond organic resins and polymers to inorganic surfaces.

As previously indicated, when a carbonyl-containing linkage of the aforementioned type is in relatively close proximity to the epoxy and hydrolyzable silyl groups of the epoxysilane, it may have the desirable effect of increasing the reactivity of these groups. Apart from any such increased reactivity, the presence of one or more of the foregoing carbonyl group-heteroatom linkages offers considerable freedom and flexibility for the synthesis of epoxysilanes of highly varied structure and properties. Since these linkages are polar, the epoxysilanes herein exhibit better solubility in polar solvents thereby expanding their breadth of uses as well as improving their adhesion to surfaces.

The epoxysilanes of this invention are well suited for use in adhesives, coatings, sealants, potting compounds, surface modification, filled composites, foundry core, glass fiber sizes and finishes, treated minerals and other applications where there is a need for a durable, high-strength, solvent-resistant coating possessing good adhesion characteristics, particularly on metal substrates.

It will be understood that all ranges stated herein include all subranges therebetween. It will also be understood that all listings of members of a group can further comprise combinations of any two or more members of the group.

In one embodiment, the epoxysilanes of the present invention are those of general Formula (1):

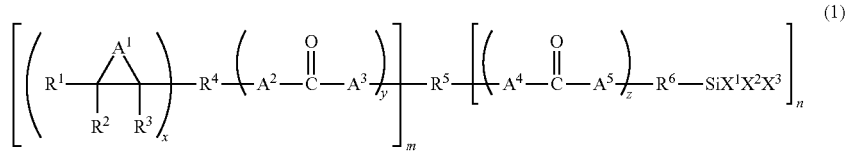

wherein:

each occurrence of $R^1$ is independently hydrogen or an alkyl group containing from 1 to 6 carbon atoms;

each occurrence of $R^2$ is independently hydrogen or a hydrocarbyl group containing from 1 to 12 carbon atoms and, optionally, at least one oxygen and/or sulfur atom, selected from the group consisting of monovalent alkyl, alkenyl, arenyl, aryl and aralkyl groups; divalent alkylene, alkenylene, arenylene, arylene and aralkylene groups in which one carbon atom of $R^2$ is covalently bonded to a carbon of the epoxy ring and the same or different carbon atom of $R^2$ is covalently bonded to a carbon atom of $R^3$ or $R^4$ to form a cyclic aliphatic structure; and polyvalent hydrocarbyl in which one carbon atom of $R^2$ is covalently bonded to a carbon atom of the epoxy ring and the same and/or different carbon atom of $R^2$ forms at least two covalent bonds with carbon atoms of $R^3$ or $R^4$ or at least one covalent bond with both $R^3$ and $R^4$ to form a bicyclic or a polycyclic aliphatic structure;

each occurrence of $R^3$ is independently hydrogen or a hydrocarbyl group containing from 1 to 12 carbon atoms and, optionally, at least one oxygen or sulfur atom, selected from the group consisting of monovalent alkyl, alkenyl, arenyl, aryl and aralkyl groups; divalent alkylene, alkenylene, arenylene, arylene and aralkylene groups in which one carbon atom of $R^3$ is covalently bonded to a carbon atom of the epoxy ring and the same or different carbon atom of $R^3$ is covalently bonded to a carbon atom of $R^2$ or $R^4$ to form a cyclic aliphatic structure; and polyvalent hydrocarbyl in which one carbon atom of $R^3$ is covalently bonded to a carbon atom of the epoxy ring and the same and/or different carbon atoms of $R^3$ form at least two covalent bonds with $R^2$ or $R^4$ or at least one covalent bond with both $R^2$ and $R^4$ to form a bicyclic or a polycyclic aliphatic structure;

each occurrence of $R^4$ is independently a divalent or polyvalent hydrocarbyl group containing up to 12 carbon atoms and, optionally, at least one oxygen or sulfur atom, selected from the group consisting of divalent alkylene, aralkylene, arenyl, arylene and aralkylene groups; and polyvalent hydrocarbyl group in which one carbon atom of $R^4$ forms a covalent bond with the carbon atom of the epoxy ring, the same or different carbon atom of $R^4$ forms a bond with a nitrogen, oxygen or sulfur heteroatom bonded to a carbonyl group, and the same or different carbon atom of $R^4$ forms at least one covalent bond with a carbon atom of $R^2$ or $R^3$ to form a bicyclic or a polycyclic structure or a heterocarbyl group containing from 2 to 12 carbon atoms and at least one heteroatom selected from oxygen or sulfur;

each occurrence of $R^5$ is independently a divalent or polyvalent hydrocarbyl group containing up to 24 carbon atoms derived by substitution of at least one hydrogen on an alkyl, alkenyl, arenyl, aryl or aralkyl group and, optionally, at least one oxygen or sulfur atom; or a divalent or polyvalent organic polymer group;

each occurrence of $R^6$ is a divalent alkylene, alkenylene, arenylene, arylene or aralkylene group containing up to 12 carbon atoms and, optionally, at least one oxygen or sulfur atom;

each occurrence of $X^1$ is independently selected from the group consisting of $R^7O—$, $R^7C(=O)O—$, $R^7{}_2C=NO—$ and $R^7{}_2NO—$ wherein each $R^7$ is independently selected from the group consisting of hydrogen or alkyl, alkenyl, arenyl, aryl and aralkyl groups wherein each $R^7$, other than hydrogen, independently contains from 1 to 18 carbon atoms and, optionally, at least one oxygen or sulfur atom;

each occurrence of $X^2$ and $X^3$ is independently selected from the group consisting of $R^8$, $R^8O—$, $R^8C(=O)O—$, $R^8{}_2C=NO—$ and $R^8{}_2NO—$ wherein each $R^8$ is independently selected from the group consisting of hydrogen or alkyl, alkenyl, arenyl, aryl and aralkyl groups wherein each $R^8$, other than hydrogen, contains from 1 to 18 carbon atoms and, optionally, at least one oxygen or sulfur atom;

each occurrence of $A^1$ is independently selected from divalent oxygen (—O—) or sulfur (—S—);

each occurrence of $A^2$ is independently selected from divalent oxygen (—O—), sulfur (—S—) or substituted nitrogen of the structure —$NR^9$— wherein $R^9$ is independently hydrogen or alkyl, alkenyl, arenyl, aryl, aralkyl or —$R^6$—$SiX^1X^2X^3$ group wherein each $R^9$, other than hydrogen, independently contains from 1 to 18 carbon atoms, and with the proviso that when $A^2$ is oxygen or sulfur, then $A^3$, infra, is —$NR^{10}$—;

each occurrence of $A^3$ is independently selected from divalent oxygen (—O—), sulfur (—S—) or substituted nitrogen of the structure —$NR^{10}$— wherein each $R^{10}$ is independently hydrogen or alkyl, alkenyl, arenyl, aryl, aralkyl or —$R^6$—$SiX^1X^2X^3$ group wherein each $R^{10}$, other than hydrogen, independently contains from 1 to 18 carbon atoms, and with the proviso that when $A^3$ is oxygen or sulfur, then $A^2$ is —$NR^9$—;

each occurrence of $A^4$ is independently selected from divalent oxygen (—O—), sulfur (—S—) or substituted nitrogen of the structure —$NR^{11}$— wherein each $R^{11}$ is independently hydrogen or alkyl, alkenyl, arenyl, aryl, aralkyl or —$R^6$—$SiX^1X^2X^3$ group wherein each $R^{11}$, other than hydrogen, independently contains from 1 to 18 carbon atoms, and with the proviso that when $A^4$ is oxygen or sulfur, then $A^5$, infra, is —$NR^{12}$—;

each occurrence of $A^5$ is independently selected from divalent oxygen (—O—), sulfur (—S—) or substituted nitrogen of the structure —$NR^{12}$— wherein $R^{12}$ is hydrogen or alkyl, alkenyl, arenyl, aryl, aralkyl or —$R^6$—$SiX^1X^2X^3$ group wherein each $R^{12}$, other than hydrogen, independently contains from 1 to 18 carbon atoms, and with the proviso that when $A^2$ is oxygen or sulfur, then $A^4$ is —$NR^{11}$—; and, each occurrence of subscripts m, n, x, y and z independently is an integer wherein m is 1 to 6; n is 1 to 6; x is 1 to 6; y is 0 or 1; and, z is 0 or 1, with the proviso that y+z is equal to or greater than 1.

As used herein in connection with the epoxysilanes of Formula (1), "alkyl" includes straight, branched and cyclic alkyl groups; "alkenyl" includes any straight, branched, or cyclic alkenyl group containing one or more carbon-carbon double bonds, where the site of substitution can be either at a carbon-carbon double bond or elsewhere in the group; "aryl" includes any aromatic hydrocarbon from which one hydrogen atom has been removed; "aralkyl" includes, but is not limited to, any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents.

Specific examples of alkyls include, but are not limited to, methyl, ethyl, propyl and isobutyl. Specific examples of alkenyls include, but are not limited to, vinyl, propenyl, allyl, methallyl, ethylidenyl norbornane, ethylidene norbornyl, ethylidenyl norbornene and ethylidene norbornenyl. Specific examples of aryls include, but are not limited to, phenyl and naphthalenyl. Specific examples of aralkyls include, but are not limited to, benzyl and phenethyl. Specific examples of arenyls include, but are not limited to, tolyl and xylyl.

As used herein in connection with epoxysilanes described by Formula (1), "cyclic alkyl", and "cyclic alkenyl" also include bicyclic, tricyclic and higher cyclic structures as well as the aforementioned cyclic structures further substituted with alkyl, and/or alkenyl groups. Representative examples of these structures include, but are not limited to, norbornyl, norbornenyl, ethylnorbornyl, ethylnorbornenyl, ethylcyclohexyl, ethylcyclohexenyl, cyclohexylcyclohexyl and cyclododecatrienyl.

In another embodiment, the epoxysilane of the present invention are those in Formula (1) wherein $R^1$, $R^2$, $R^3$, $R^4$, $A^2$, $A^3$, $A^4$ and $A^5$ have the aforestated meanings; $R^5$ is specially a hydrocarbon of from 1 to 12 carbon atoms, more specially from 2 to 6 carbon atoms and most specially, 3 carbon atoms; $R^6$ is specially a hydrocarbon of from 1 to 12 carbon atoms, more specially from 2 to 6 carbon atoms and most specially, 3 carbon atoms; $A^1$ is specially oxygen or sulfur and more specially oxygen; $X^1$ is $OR^7$ wherein each $R^7$ is independently selected from the group consisting specially of hydrogen, methyl, ethyl, isopropyl, n-propyl, 1-propenyl, phenyl, tolyl, and benzyl and more specially from hydrogen, methyl and ethyl; $X^1$ and $X^2$ is $R^8$ or $OR^8$ wherein each $R^8$ is independently selected from the group consisting specially of hydrogen, methyl, ethyl, isopropyl, n-propyl, 1-propenyl, phenyl, tolyl, and benzyl and more specially from hydrogen, methyl and ethyl; m is specifically from 1 to 4 and more specifically 1; n is specially from 1 to 4 and more specifically 1; x is 1; y is specifically 0 or 1 and more specifically 0; z is 1. In yet another embodiment, m is from 2 to 4 and n is specifically from 1 to 4 and more specifically 2.

In still another embodiment, $R^5$ is a divalent or polyvalent organic polymer group, selected from polyester; polyalkenylene oxide; polyolefin; polyurethane, phenolic, polysulfides, and homopolymers and copolymers of styrene, vinyl acetate, alkyl acrylate and methacrylate, acrylonitrile, allyl chloride, allyl alcohol, alkene, diene, and the like.

The epoxysilane of the present invention that contain a single epoxy group and a single hydrolyzable group are particularly useful as coupling agents, adhesion promoters and silylating agent for organic polymers.

The epoxysilane of the present invention that two or more epoxy functional groups and one or more hydrolyzable silyl groups are particularly useful as intermediates for coating, potting compounds, composite resins, and the like. The epoxysilanes of the present invention with two or more epoxy functional groups and one or more hydrolyzable silyl groups allow for dual curing resin. These epoxy silanes can be mixed with other resins, especially other epoxy resins, to control the crosslink density, brittleness and strength of the cured resin. The curatives commonly used and other conditions necessary to use these epoxysilanes as resins or resin additives are described in, e.g., "Handbook of Epoxy Resins", H. Lee and K. Neville, McGraw-Hill Book Company, New York (1967).

The epoxysilane of the present invention that contain an episulfide group are useful as additives and coupling agents for sulfur cured elastomers or polysulfide polymer systems. The episulfide more easily reacts with sulfur or mercaptan groups during the curing reactions.

When the epoxysilane of the present invention is a polymeric material, they are useful as resins and as additives to resin systems, especially epoxy resins, as impact modifiers and flexibilizers.

Particularly useful epoxysilanes in accordance with the invention are the non-limiting examples selected from the group consisting of N-(3-trimethoxysilylpropyl)carbamic acid oxiranyl methyl ester; 3-triethoxysilylpropyl-carbamic acid oxiranyl methylester; [3-(triethoxysilyl)propyl]-carbamic acid oxiranyl nonadecyl ester; [3-(triethoxysilyl)propyl]-carbamic acid 2-[2-(2-methoxyethoxy)ethoxy]oxiranyl ethyl ester; carbonic acid 1,1-dimethylethyl 3-[[[[3-(triethoxysilyl)propyl]amino]carbonyl]oxy]oxiranyl phenyl ester; [3-(triethoxysilyl)propyl]-carbamic acid oxiranyl-3-phenyl-2-propenyl ester; [3-(triethoxysilyl)propyl]-carbamic acid oxiranyl-3,3-diphenyl-3H-naphtho[2,1-b]pyran-9-yl ester; [3-(ethoxydimethoxysilyl)propyl]-carbamic acid oxiranyl methyl ester; [3-(diethoxymethoxysilyl)propyl]-carbamic acid oxiranyl methyl ester; [3-(triethoxysilyl)propyl]-carbamic acid oxiranyl-3,3,4,4,5,5,6,6,7,7,8,8,8-tridecafluorooctyl ester; [3-(triethoxysilyl)propyl]-carbamic acid oxiranyl-1,3,5-benzenetriyltris(methylene) ester; [3-

(triethoxysilyl)propyl]-carbamic acid oxiranyl-1,3,5-benzenetriyltris(methylene) ester; [3-(triethoxysilyl)propyl]-carbamic acid oxiranyl-phenylmethyl ester; [3-(trimethoxysilyl)propyl]-carbamic acid oxiranyl ethyl ester; [3-(trimethoxysilyl)propyl]-carbamic acid oxiranyl-1,1-dimethylethyl ester; [3-(triethoxysilyl)propyl]-carbamic acid oxiranyl-1,1-dimethylethyl ester; [3-(trimethoxysilyl)propyl]-carbamic acid oxiranyl methyl ester; [3-(triethoxysilyl)propyl]-carbamic acid oxiranyl ethyl ester; and combinations thereof.

Particularly useful epoxysilanes in accordance with the invention in which the epoxysilanes contains two or more epoxy functional groups and at least one hydrolyzable silyl group are the non-limiting examples selected from the group consisting of (3,4-bis-oxiranylmethoxycarbonylamino-phenyl)-carbamic acid 2-(dimethoxy-methyl-silanyl)-ethyl ester; [3-(diethoxy-methyl-silanyl)-propyl]-carbamic acid 3-oxiranylmethylcarbamoyloxy-2-oxiranylmethylcarbamoyloxymethyl-propyl ester; [3-(triethoxysilanyl)-propyl]-carbamic acid 2-oxiranylmethoxy-1-oxiranylmethoxymethyl-ethyl ester; (3-triethoxysilanyl-propyl)-carbamic acid 3-oxiranylmethoxy-2-oxiranylmethoxymethyl-2-(3-triethoxysilanyl-propylcarbamoyloxymethyl)-propyl ester; (2-{2-[2-(2-oxiranylmethoxycarbonylamino-ethoxy)-ethoxy]-3-[(3-triethoxysilanyl-propylcarbamoyl)-methoxy]-propoxy}-ethyl)-carbamic acid oxiranylmethyl ester; and the like The epoxysilanes of this invention can be prepared by any of several synthetic processes including those hereinafter described.

Synthetic Process 1: Reaction of Epoxy Alcohol with Isocyanatosilane to Provide Epoxysilane Epoxy alcohol is reacted with isocyanatosilane under suitable conditions, e.g., under anhydrous condition, at subambient, ambient or elevated temperatures, at reduced, atmospheric or high pressures, and in the presence or absence of solvent(s) and/or catalyst(s), to provide epoxysilane of the invention. Anhydrous conditions specifically include under dry air, more specifically under an inert atmosphere such as a blanket of nitrogen, to prevent the premature hydrolysis of the hydrolyzable silyl group(s). Typical temperatures used in preparing the epoxysilane include the non-limiting range of from about 0° to about 150° C., more specifically from about 25° to about 100° C. and most specifically from about 60° to about 90° C. Typical pressures used in the preparation of the epoxysilane include the non-limiting range of from about 0.1 mm Hg to about 10 bars, more specifically from about 10 mm Hg to 2 bars and most specifically from about 600 mm Hg to about 1 bar. Typical solvents used in the preparation of the epoxysilanes are aprotic solvents such as ethers, esters, ketones, chlorinated hydrocarbons and hydrocarbons. Representative non-limiting examples of useful solvents are ethyl ether, tetrahydrofuran, acetone, ethyl acetate, chloroform, methylene chloride, toluene, hexanes, cyclohexanes, and the like. Catalysts that can be employed to facilitate the reaction are those typically used to promote the reaction of alcohols with isocyanates. These catalysts include the non-limiting examples of transition metal salts, dialkyltin carboxylates such as dibutyltin diacetate and dibutyltin dilaurate, stannous salts of carboxylic acids such as stannous octanoate and stannous acetate, stannous oxides, bismuth salts and tertiary amines.

In one embodiment, the epoxy alcohol reactant conforms to general Formula (2):

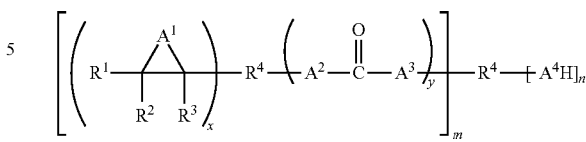

wherein $R^1$, $R^2$, $R^3$, $R^4$, $R^5$, $A^1$, $A^2$ and $A^3$ have the aforestated meanings, $A^4$ is oxygen or sulfur, x is 1, y is 0, m is 1 and n is 1.

Useful epoxy alcohol reactants of Formula (2) include those in which $R^1$, $R^2$ and $R^3$ are hydrogen, $R^4$ is a hydrocarbyl group containing from 1 to 12 carbon atoms and, optionally, at least one oxygen or sulfur atom, each $A^1$, $A^2$ and $A^3$ is oxygen or sulfur, e.g., glycidol, 3,4-epoxybutan-1-ol and 1,2-epoxy-3-mercaptopropane; those in which $R^2$, $R^3$ and/or $R^4$ are joined together and with the epoxide ring form cycloaliphatic epoxy alcohols such as those disclosed in U.S. Pat. No. 6,268,403, the entire contents of which are incorporated by reference herein; and, hydroxyl or mercapto group-containing episulfides (also known as thiirenes or alkylene sulfides) such as those disclosed in U.S. Pat. No. 3,622,597, the entire contents of which are also incorporated by reference herein.

Specific examples of useful cycloaliphatic epoxyalcohols are:

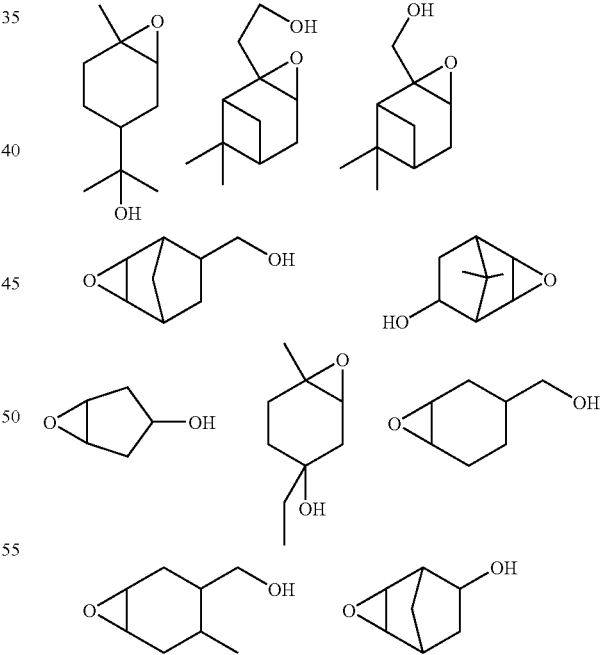

Specific examples of useful epoxy alcohols possessing the episulfide ring are 2,3-episulfide-1-propanol, 3,4-episulfide-1-butanol, 4,5-episulfide-1-pentanol, 4,5-episulfide-2-pentanol, 5,6-episulfide-1-hexanol and 5,6-episulfide-2-hexanol.

In another embodiment, a useful epoxy alcohol reactant is one of general Formula (3):

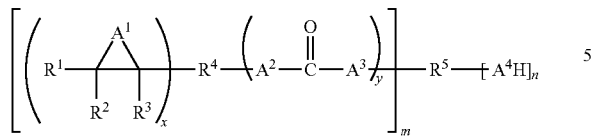
(3)

wherein $R^1$, $R^2$, $R^3$, $R^4$, $R^5$, $A^1$, $A^2$, $A^3$, m and n have the aforestated meanings, each $A^4$ is oxygen or sulfur, m is 1, n is 1 to 6, x is 2 to 6, y is 0 and n is 1 to 6.

An epoxy alcohol of Formula (3) can be readily obtained by reacting polyhydric alcohol of Formula (4)

$$R^{13}(A^2H)_{m+n} \quad (4)$$

wherein $R^{13}$ is a divalent or polyvalent hydrocarbon group continuing from about 2 to 34 carbon atoms and, optionally, at least one oxygen or sulfur, $A^2$ is oxygen or sulfur and m and n have the aforestated meanings, e.g., ethylene glycol, diethylene glycol, propylene glycol, dipropylene glycol, glycerol, pentaerythritol, polyether diol, polyether thiol, etc., with an epihalohydrin, in particular epichlorohydrin or epibromohydrin, the stoichiometrics, reaction procedures and reaction conditions being such as to favor the production of the desired epoxy alcohol. For example, two moles of epichlorohydrin will preferentially react with the two primary hydroxyl groups of glycerol according to the following equation to provide epoxy alcohol (5) containing two epoxy groups and one hydroxyl group as shown below:

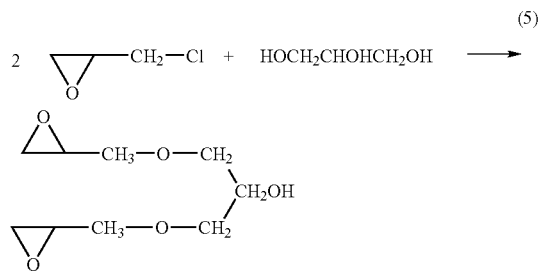
(5)

Similarly, a ratio of two or three moles of epichlorohydrin per mole of pentaerythritol will provide epoxy alcohol (6) and/or (7) respectively:

(6)

(7)

In one embodiment, the isocyanatosilane reactant employed in Synthetic Process 1 conforms to general Formula (8):

$$O{=}C{=}N{-}R^6{-}SiX^1X^2X^3 \quad (8)$$

wherein $R^6$, $X^1$, $X^2$ and $X^3$ each have the aforestated meanings.

Specific isocyanatosilanes (8) that can be used herein include isocyanatopropyltrimethoxysilane, isocyanatoisopropyltrimethoxysilane, isocyanato-n-butyltrimethoxysilane, isocyanato-t-butyltrimethoxysilane, isocyanatopropyltriethoxysilane, isocyanatoisopropyltriethoxysilane, isocyanato-n-butyltriethoxysilane, isocyanato-t-butyltriethoxysilane, and the like.

The epoxysilanes resulting from Synthetic Process 1 are represented by general Formula (1):

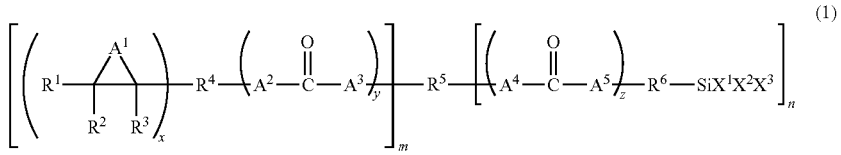
(1)

wherein $R^1$, $R^2$, $R^3$, $R^4$, $R^5$, $R^6$, $A^1$, $A^2$, $A^3$, $X^1$, $X^2$, $X^3$ and n have the aforestated meanings and $A^4$ is oxygen or sulfur and $A^5$ is —NH—, m is 1, x is 1 to 6, y is 0 and z is 1.

Some examples of epoxysilanes that can be obtained by Synthetic Process 1 are:

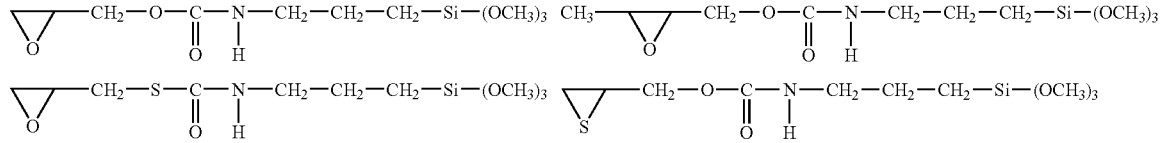

-continued

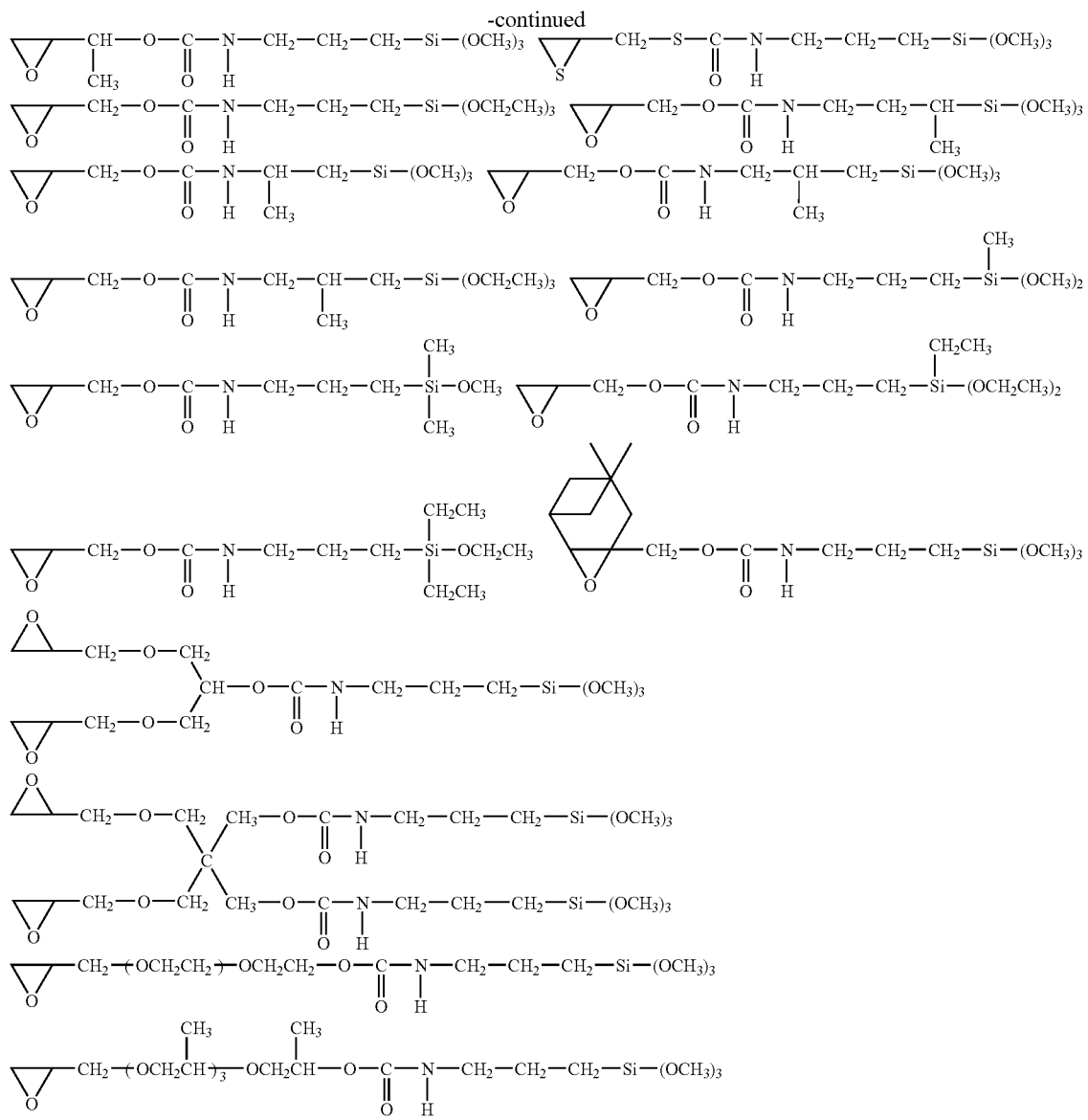

Synthetic Process 2: Reaction of Epoxy Alcohol with Polyisocyanate to Provide Epoxyisocyanate Intermediate Followed by Reaction of Epoxyisocyanate Intermediate with Secondary Aminoalkoxysilane and/or Mercaptoalkoxysilane to Provide Epoxysilane.

Epoxy alcohol is reacted with polyisocyanate in a first step under suitable conditions, e.g., under anhydrous conditions, at subambient, ambient or elevated temperature, at reduced, atmospheric or high pressure and in the presence or absence of solvent(s) and/or catalyst(s), to provide epoxy-isocyanate intermediate which is then reacted with secondary aminoalkoxysilane and/or mercaptoalkoxysilane in a second step to provide epoxysilane possessing at least one urethane linkage.

First Step: Reaction of Epoxy Alcohol with Polyisocyanate to Provide Intermediate Epoxyisocyanate Intermediate In one embodiment, the epoxy alcohol employed in the first step of Synthetic Process 2 can be one or more of general Formulas (2) and/or (3), supra.

The polyisocyanate can be any aromatic, aliphatic or cycloaliphatic polyisocyanate, e.g., diisocyanate or triisocyanate, including isocyanate-terminated prepolymers prepared from such polyisocyanates.

In one embodiment, the polyisocyanate reactant (inclusive of isocyanate-terminated prepolymers) is represented by general Formula (9):

$$(O=C=N)_{m+n}R^5 \qquad (9)$$

wherein $R^5$, m and n have the aforestated meanings.

Examples of suitable aromatic polyisocyanates are any of the isomers of toluene diisocyanate (TDI), either in pure isomer form or in the form of a mixture of several isomers, naphthalene-1,5-diisocyanate, diphenylmethane-4,4'-diisocyanate (MDI), diphenylmethane-2,4'-diisocyanate and mixtures of 4,4'-diphenylmethane diisocyanate with the 2,4' isomer or mixtures thereof with oligomers of relatively high functionality (so-called crude MDI). Examples of suitable cycloaliphatic polyisocyanates are the hydrogenation products of the above-mentioned aromatic diisocyanates such as, for example, 4,4'-dicyclohexylmethane diisocyanate, 1-isocyanatomethyl-3-isocyanto-1,5,5-trimethyl cyclohexane (isophorone diisocyanate, IPDI), cyclohexane-1,4-diisocyanate, hydrogenated xylylene diisocyanate, m- or p-tetramethyl xylylene diisocyanate (m-TMXDI, p-TMXDI)), trimethylhexamethylene diiscyanate (TMDI, commercially available as a blend of the isomers 1,6-diisocyanato-2,2,4-trimethylhexane and 1,6-diisocyanato-2,4,4-trimethylhexane) and dimer fatty acid diisocyanate.

Of the foregoing polyisocyanates, those possessing isocyanate groups of different reactivity, e.g., TDI, IPDI and TMDI, are preferred since they will tend to leave the more slowly reacting isocyanate group(s) intact thereby minimizing the production of epoxy compounds possessing no free isocyanate groups. However, to the extent such epoxy compounds may be produced, they need not be separated from the epoxyisocyanate intermediates since their epoxy functionality will also contribute to the usefulness of the second step epoxysilanes for application as adhesion promoters, coating intermediates, crosslinkers, and the like.

Organic $R^5$ group of polyisocyanate (9) can be polymeric in nature as in the case of the aforementioned isocyanate-terminated prepolymers. Such polymers are typically prepared by reacting a molar excess of polyisocyanate, typically a diisocyanate such as MDI or IPDI, with a polyol, e.g., a polyether diol such as the ethylene oxide and/or propylene oxide adducts of a $C_2$-$C_4$ diol, a polytetramethylene diol, a polyester diol derived from the reaction of a $C_2$-$C_4$ diol initiator and a lactone such as gamma-butyrolactone or episilon-caprolactone, a dihydroxyl-terminated hydrocarbon such as a dihydroxyl-terminated hydrogenated polybutadiene, and the like.

Suitable reaction conditions for the first step of Synthetic Process 2 include anhydrous conditions, specifically including under dry air, more specifically under an inert atmosphere such as a blanket of nitrogen, to prevent the premature hydrolysis of the epoxy-isocyanate intermediate of the first step and hydrolyzable silyl group(s) of the epoxysilane product of the second step. Typical temperatures used in preparing the epoxy-isocyanate intermediate include the non-limiting range of from about 0° to about 150° C., more specifically from about 25° to about 100° C. and most specifically from about 60° to about 90° C. Typical pressures used in the preparation of the epoxy-isocyanate intermediate include the non-limiting range of from about 0.1 mm Hg to about 10 bars, more specifically from about 10 mm Hg to about 2 bars and most specifically from about 600 mm Hg to about 1 bar. Typical solvents that can be used in the preparation of the epoxy-isocyanate intermediate are aprotic solvents such as ethers, esters, ketones, amides, chlorinated hydrocarbons and hydrocarbons. Representative non-limiting examples of useful solvents are ethyl ether, tetrahydrofuran, acetone, ethyl acetate, chloroform, methylene chloride, toluene, hexanes, cyclohexanes, and the like. Catalysts are often used to facilitate this type of reaction and include those typically used to promote the reaction of alcohols with isocyanates. Suitable catalysts include the non-limiting examples of transition metal salts, dialkyltin carboxylates such as dibutyltin diacetate and dibutyltin dilaurate, stannous salts of carboxylic acids such as stannous octanoate and stannous acetate, stannous oxides, bismuth salts and tertiary amines.

Reaction of epoxy alcohol of general Formulas (2) and/or (3) and polyisocyanate or isocyanate-terminated prepolymer (9) provides epoxy-isocyanate intermediate(s) represented, respectively, by general Formula (10):

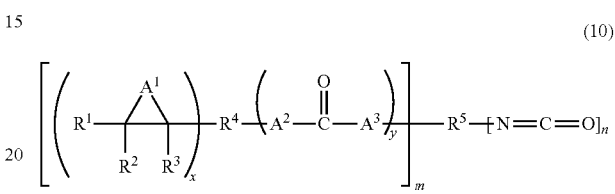

(10)

wherein each $R^1$, $R^2$, $R^3$, $R^4$, $R^5$, $A^1$, m, and n have the aforestated meanings, $A^2$ is oxygen or sulfur, $A^3$ is —NH—, x is 1 to 6 and y is 1.

In one embodiment, reaction of epoxy alcohol (2) and diisocyanate or isocyanate-terminated prepolymer derived from a diol (corresponding to general Formula (9) wherein m+n is 2) provides epoxy-isocyanate intermediate (10) wherein $R^1$, $R^2$, $R^3$, $R^4$, $R^5$, and $A^1$ have the aforestated meanings, $A^2$ is oxygen or sulfur, $A^3$ is —NH—, m is 1, n is 1, x is 1 and y is 1.

In another embodiment, reaction of epoxy alcohol (3) with diisocyanate or isocyanate prepolymer provides epoxy-isocyanate intermediate (10)

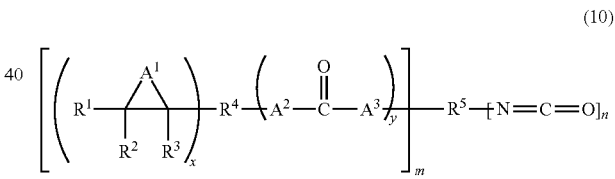

(10)

wherein $R^1$, $R^2$, $R^3$, $R^4$, $R^5$ and $A^1$ have the aforestated meanings, $A^2$ is oxygen or sulfur, $A^3$, is —NH—, m is 1, n is 1, x is 2 to 6 and y is 1.

Some epoxy-isocyanate intermediates that can be prepared in accordance with the first step of Synthetic Process 2 are:

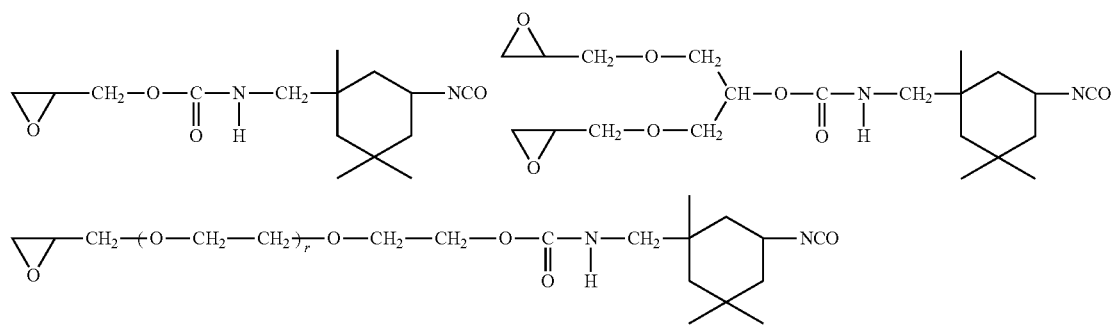

-continued

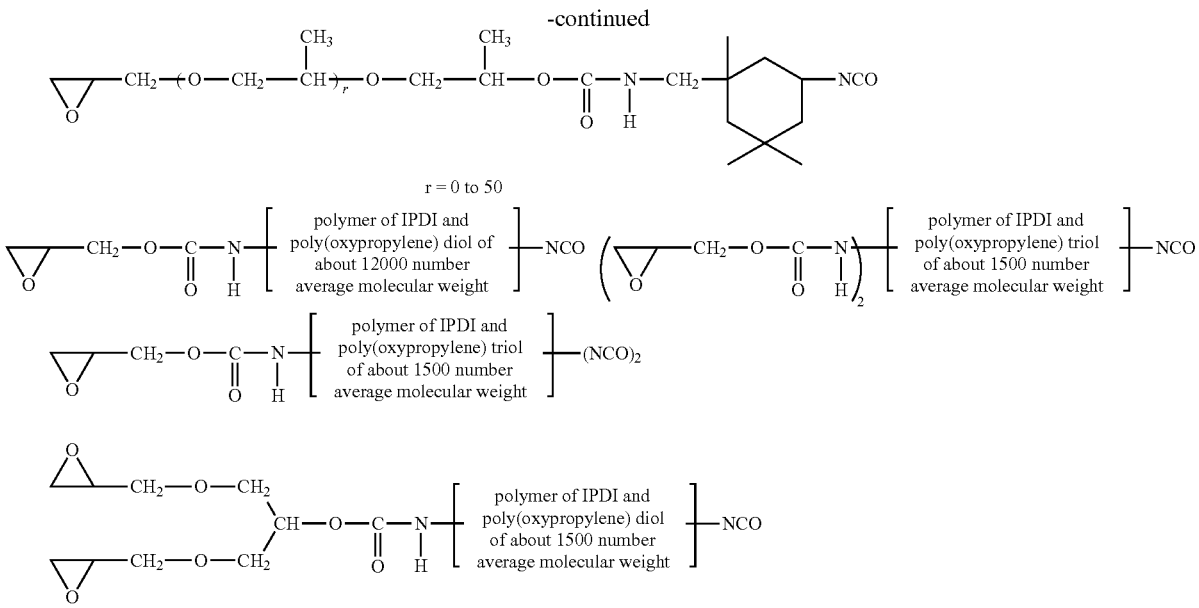

Second Step: Reaction of Epoxyisocyanate Intermediate with Secondary Aminoalkoxysilane and/or Mercaptoalkoxysilane to Provide Epoxysilane In the second step of Synthetic Process 2, epoxy-isocyanate intermediate resulting from the first step, e.g., epoxy-isocyanate (10), is reacted with secondary aminoalkoxysilane and/or mercaptoalkoxysilane under anhydrous conditions at reduced, atmospheric or high pressure, at sub-ambient, ambient or elevated temperature, in the presence or absence of solvents to provide one or more epoxysilanes according to the invention.

In one embodiment, the hydrolyzable silane reactant employed in the second step of Synthetic Process 2 is represented by general Formula (11):

wherein $R^6$, $X^1$, $X^2$ and $X^3$ have the aforestated meanings and $A^5$ is sulfur or —N($R^{12}$)— in which $R^{12}$ is an alkyl, arenyl, arenyl, aryl, aralkyl or —$R^6SiX^1X^2X^3$ group in which each $R^{12}$ independently contains from 1 to 18 carbon atoms.

Useful secondary aminoalkoxysilane reactants of Formula (11) include N-methylaminopropyltrimethoxysilane, N-ethylaminopropyltrimethoxysilane, N-phenylaminopropyltrimethoxysilane, N-methylaminobutyltrimethoxysilane, N-methylaminoisobutyltrimethoxysilane, N-methylaminopropyltrimethoxysilane, N-methylaminobutyltriethoxysilane, N-methylaminopropylmethoxydiethoxysilane, N-methylaminopropyldimethylmethoxysilane, N-methylaminobutylethyldiethoxysilane; N-methylaminobutyldiethylethoxysilane, N,N-bis[(3-trimethoxysilyl)propyl]amine, N,N-bis[(3-trimethoxysilyl)butyl]amine, N,N-bis[(3-trimethoxysilyl)isobutyl]amine, N,N-bis[(3-triethoxysilyl)propyl]amine, N,N-bis[(3-triethoxysilyl)butyl]amine, and the like.

Useful mercaptoalkoxysilane reactants of Formula (11) include gamma-mercaptopropylmethyldimethoxysilane, gamma-mercaptopropyltrimethoxysilane, gamma-mercaptopropylmethyldiethoxysilane, gamma-mercaptopropyltriethoxysilane, gamma-mercaptopropylethyldimethoxysilane, gamma-mercaptopropylethyldiethoxysilane, beta-mercaptopropyldimethylmethoxysilane, beta-mercaptoethylmethyldimethoxysilane, beta-mercaptoethyltriethoxysilane, and the like.

In general, reaction of epoxy-isocyanate intermediate (10) with hydrolyzable silane (11) will be carried out in such a manner as to provide one or more epoxysilanes of this invention wherein substantially all of the free —NCO group(s) of these intermediates have been converted to urea linkage(s) when alkoxysilane (11) is one or more secondary aminoalkoxysilanes, thiocarbamate linkage(s) when alkoxysilane (11) is one or more mercaptoalkoxysilanes, or mixture of urea and thiocarbamate linkage(s) when a mixture of secondary aminoalkoxysilane(s) and mercaptoalkoxysilane(s) is employed. Suitable reaction conditions for accomplishing the second step of Synthetic Process 2 include, e.g., anhydrous conditions, at sub-ambient, ambient or elevated temperatures, reduced, atmospheric or high pressures and in the absence or presence of catalysts. The reaction of the secondary aminosilane with the epoxy-isocyanate intermediate typically does not require a catalyst although the catalysts used in the preparation of the epoxy-isocyanate intermediate in the first step will also increase the rate of reaction in the second step. Thus, the reaction of mercaptosilanes with the epoxy-isocyanate intermediate will ordinarily benefit from the use of a catalyst. Typically, bases and metal salts or their complexes can be used including the non-limiting examples of tertiary amines such as triethyl amine, triisopropyl amine and pyridine, metal oxides such as potassium oxide and stannous oxide, metal alkoxides such as potassium alkoxide, titanium tetraethoxide and titanium tetraisopropoxide and metal carboxylates such as dibutyltin dilaurate, dibutyltin diacetate, stannous acetate, bismuth acetate, zirconium acetate, and the like. Solvents are particularly useful when the epoxy-isocyanate intermediate or epoxysilane have high viscosity. Aprotic solvents which do not readily react with the secondary aminosilane or mercaptosilane can be used and include as non-limiting examples hydrocarbons, ethers and esters. Representative examples of these solvents include toluene, hexanes, decanes, cyclohexane, ethyl acetate, tetrahydrofuran, diethyl ether, 1,2-dimethoxyethane, and the like.

Epoxysilanes resulting from Synthetic Process 2 are represented, respectively, by general Formulas (1)

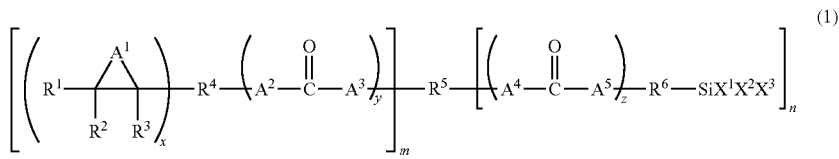

wherein $R^1$, $R^2$, $R^3$, $R^4$, $R^5$, $R^6$ and $A^1$ have the aforestated meanings, $A^2$ is oxygen or sulfur, each of $A^3$ and $A^4$ is —NH—, $A^5$ is sulfur or —$NR^{12}$— wherein $R^{12}$ is an alkyl, alkenyl, arenyl, aryl, aralkyl or —$R^6$—$SiX^1X^2X^3$ group containing 1 to 18 carbon atoms, x is 1 to 6, y is 1, z is 1, m is 1 to 6 and n is 1 to 6.

Some examples of epoxysilanes that can be obtained by Synthetic Process 2 are:

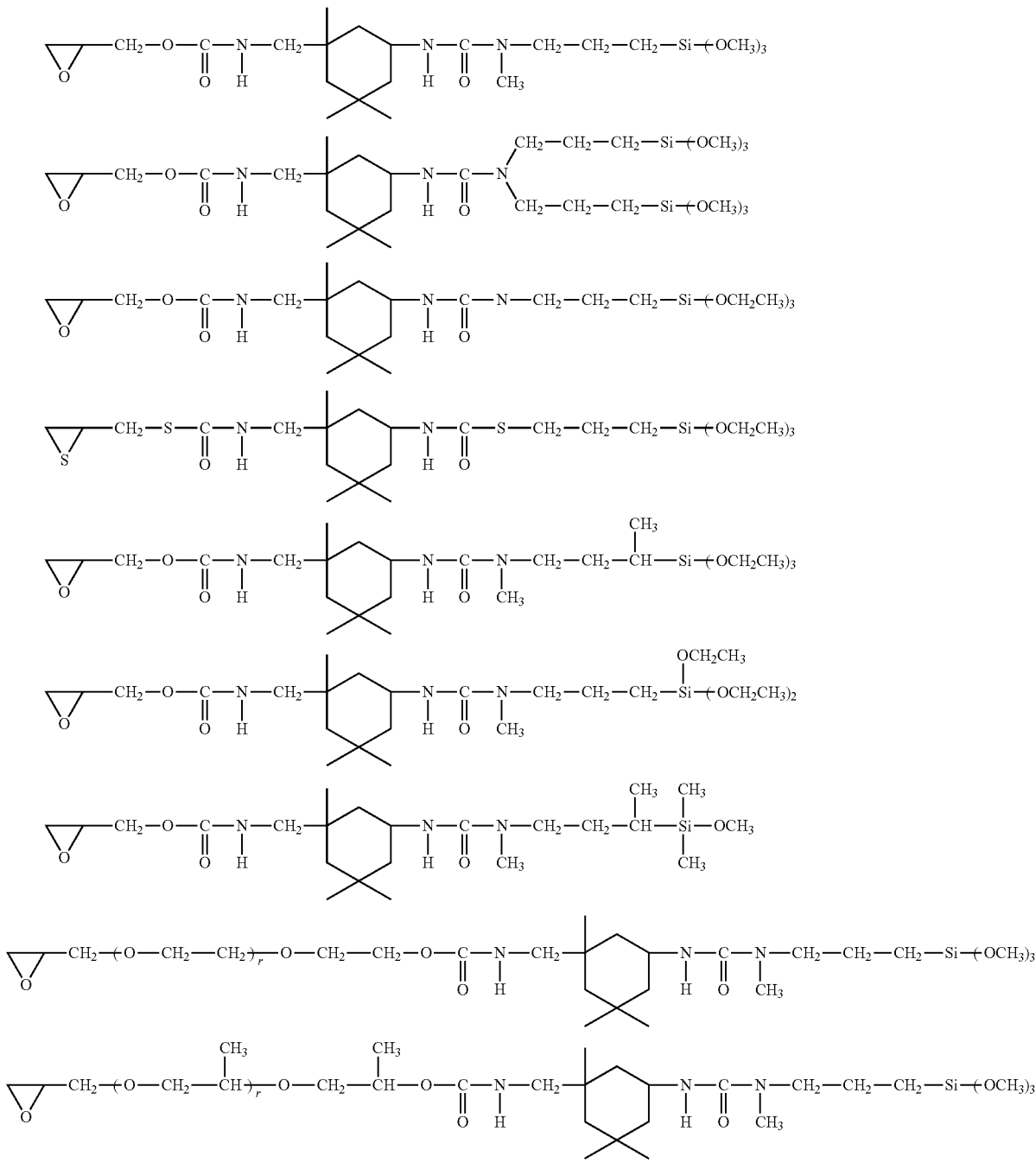

-continued

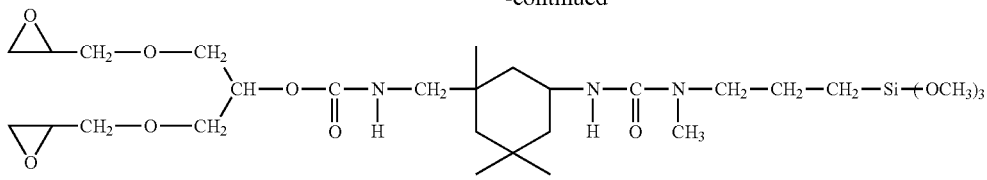

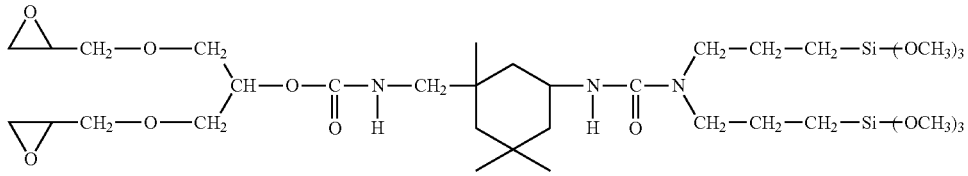

Synthetic Process 3: Reaction of Polyisocyanate with Aminoalkoxysilane and/or Mercaptoalkoxysilane to Provide Isocyanatosilane Followed by Reaction of Isocyanatosilane with Epoxy Alcohol to Provide Epoxysilane Synthetic Process 3 can be considered a variation of Synthetic Process 2. While the reactants are the same, the order of their reaction is different. Thus, in accordance with Synthetic Process 3, polyisocyanate is reacted in a first step with aminoalkoxysilane and/or mercaptoalkoxysilane under similar conditions as described above to provide intermediate isocyanatosilane which is then reacted with epoxy alcohol in a second step to provide epoxysilane in accordance with the invention.

First Step: Reaction of Polyisocyanate with Aminoalkoxysilane and/or Mercaptoalkoxysilane to Provide Isocyanatosilane Intermediate In one embodiment, polyisocyanate of general Formula (9) is reacted with aminoalkoxysilane and/or mercaptoalkoxysilane of general Formula (11) to provide isocyanatosilane intermediate of general Formula (12):

$$[O=C=N]_{m}-R^5-\left[\left(A^4-\overset{O}{\underset{\|}{C}}-A^5\right)_{z}-R^6-SiX^1X^2X^3\right]_n \quad (12)$$

wherein $R^5$ and $R^6$ have the aforestated meanings and $A^4$ is —$NR^7$—, wherein $R^7$ is hydrogen, $A^5$ is sulfur or —$NR^{12}$—, wherein $R^{12}$ is alkyl, alkenyl, arenyl, aryl, aralkyl or —$R^{61}SiX^1X^2X^3$ group containing 1 to 18 carbon atoms, m is 1 to 6, n is 1 to 6 and z is 1.

As in the case of the first step of Synthetic Process 3 which may employ a polyisocyanate possessing isocyanate groups of significantly different reactivity so as to minimize production of product(s) possessing no free isocyanate, it may also be advantageous to employ one or more of such polyisocyanates, e.g., TDI, IPDI and/or TMDI, in the first step of Synthetic Process 3 to accomplish the same result.

Some examples of isocyanatosilane intermediate (12) are:

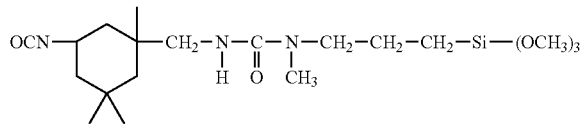

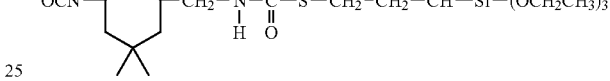

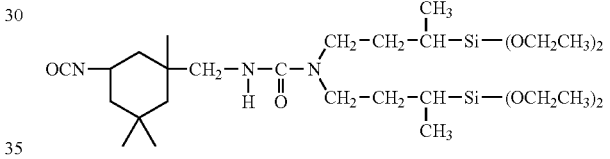

Second Step: Reaction of Isocyanatosilane Intermediate with Epoxy Alcohol to Provide Epoxysilane Isocyanatosilane intermediate (12) from the first step of Synthetic Process 3 is reacted with epoxy alcohol, e.g., of general Formula (2) and/or (3), under reaction conditions described above to provide epoxysilane(s) in accordance with the invention.

When epoxy-isocyanate intermediate (10) of Synthetic Process 2 and isocyanatosilanes intermediates (12) of Synthesis Process 3 are prepared from the same polyisocyanates (9) whose isocyanate functionalities are substantially equal in reactivity toward active hydrogen-containing species, depending on the reactants employed in the second step of each of these processes, i.e., hydrolyzable silane (11) in the case of Synthetic Process 2 and epoxy alcohol (2) and/or (3) in the case of Synthetic Process 3, the resulting epoxysilanes may be identical. However, it will be noted that when the aforestated intermediates are prepared from polyisocyanates whose isocyanate groups differ significantly in reactivity, e.g., IPDI, depending on the reactants employed in the second step of each process, Synthetic Process 3 may result in epoxysilanes that are geometric isomers of the epoxysilanes resulting from Synthetic Process 2.

Some examples of epoxysilanes that can be prepared in accordance with Synthetic Process 3 are:

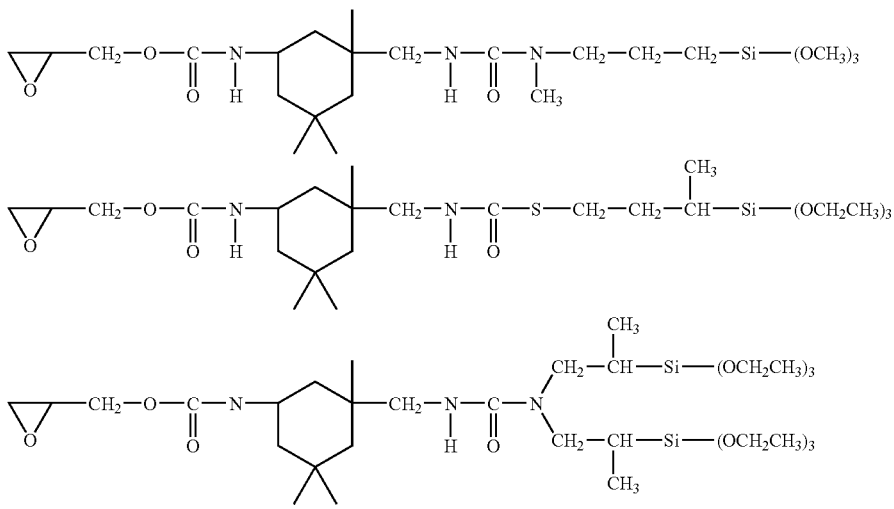

Synthetic Process 4: Reaction of Epoxy Alcohol with Ethylenically Unsaturated Isocyanate to Provide Ethylenically Unsaturated Epoxide Intermediate which is then Reacted with Hydridoalkyalkoxysilane to Provide Epoxysilane Epoxy alcohol is reacted in a first step with ethylenically unsaturated isocyanate under suitable conditions, e.g., anhydrous conditions, at sub-ambient, ambient or elevated temperatures, reduced, atmospheric or high pressures and in the absence or presence of catalysts and solvents, to provide ethylenically unsaturated epoxide intermediate which is then reacted in a second step with hydridoalkoxysilane under suitable reaction conditions, e.g., anhydrous conditions at ambient or elevated temperatures, reduced, atmospheric or high pressures, in the presence of a hydrosilation catalyst and optionally solvents, to provide epoxysilane in accordance with the invention.

First Step: Reaction of Epoxy Alcohol with Ethylenically Unsaturated Isocyanate to Provide Ethylenically Unsaturated Epoxide Intermediate In accordance with Synthetic Process 4, epoxy alcohol (2) and/or (3) is reacted with ethylenically unsaturated isocyanate (13):

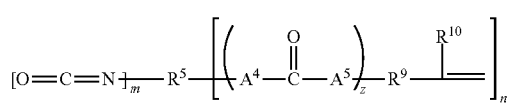

(13)

wherein $R^5$ has the aforestated meaning, $A^4$ is —NH—, $A^5$ is oxygen or —NR$^{12}$—, wherein $R^{12}$ is an alkyl, arenyl, aryl, aralkyl or —$R^6SiX^1XX^2X^3$ group containing 1 to 18 carbon atoms, $R^{13}$ is alkylene, arenylene, arylene or aralkylene of from 1 to 10 carbon atoms, $R^{14}$ is alkyl, arenyl, aryl or aralkyl group containing 1 to 8 carbon atoms, with the proviso that the sum of the carbon atoms of $R^{13}$ and $R^{14}$ is less than or equal to 12, in a first step to provide ethylenically unsaturated epoxide intermediate (14):

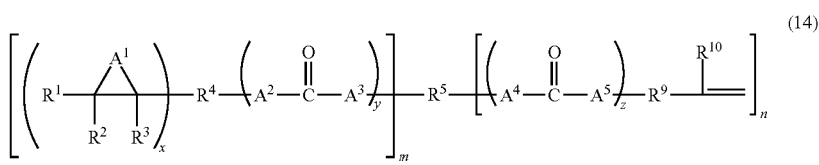

(14)

wherein $R^1$, $R^2$, $R^3$, $R^4$, $R^5$, $R^6$, $R^{13}$ and $R^{14}$ have the aforestated meanings, $A^1$ and $A^2$ are oxygen, $A^3$ and $A^4$ are —NH—, $A^5$ is oxygen or —NR$^{12}$—, wherein $R^7$ is alkyl, arenyl, aryl, aralkyl or —$R^6SiX^1X^2X^3$ group containing up to 18 carbon atoms, x is 1 to 6, y is 1, z is 0 or 1, m is 1 to 6 and n is 1 to 6.

Some specific examples of useful ethylenically unsaturated isocyanates (13) include vinyl isocyanate, allyl isocyanate, 3-isocyanate-2-methyl-propene, vinylbenzyliisocyanate, 3-isocyanate-1-butene, 3-isocyanate-3-methyl-1-butene, 4-isocyanate-2-methyl-1-butene, 4-isocyanate-3,3-dimethyl-1-butene, 4-isocyanate-4-methyl-1-pentene and 5-isocyanate-1-pentene. Taking commercial availability into account, the preferred isocyanates are methallyl isocyanate and allyl isocyanate.

Anhydrous conditions specifically include under dry air, more specifically under an inert atmosphere such as a blanket of nitrogen, to prevent the premature hydrolysis of the hydrolyzable silyl group(s). Typical temperatures used in preparing the epoxysilane include the non-limiting range of from about 0° to about 150° C., more specifically from about 25° to about 100° C. and most specifically from about 60° to about 90° C. Typical pressures used in the preparation of the epoxysilane include the non-limiting range of from about 0.1 mm Hg to about 10 bars, more specifically from about 10 mm Hg to 2 bars and most specifically from about 600 mm Hg to about 1 bar. Typical solvents used in the preparation of the epoxysilanes are aprotic solvents such as ethers, esters, ketones, chlorinated hydrocarbons and hydrocarbons. Representative non-limiting examples of useful solvents are ethyl ether, tetrahydrofuran, acetone, ethyl acetate, chloroform, methylene chloride, toluene, hexanes, cyclohexanes, and the like. Catalysts that can be employed to facilitate the reaction are those typically used to promote the reaction of alcohols with isocyanates. These catalysts include the non-limiting examples of transition metal salts, dialkyltin carboxylates such as dibutyltin diacetate and dibutyltin dilaurate, stannous salts of carboxylic acids such as stannous octanoate and stannous acetate, stannous oxides, bismuth salts and tertiary amines.

Second Step: Reaction of Ethylenically Unsaturated Epoxide Intermediate with Hydridoalkoxysilane to Provide Epoxysilane In the second step of Synthetic Process 4, ethylenically unsaturated epoxide intermediate from the first step is hydrosilated with hydridoalkoxysilane (15) to provide epoxysilane of general Formula (1). Because many hydrosilation catalysts are poisoned by sulfur-containing materials, intermediate (14) should be free of sulfur atoms. The conditions for hydrosilation of intermediates containing carbon-carbon double bonds is well known in the art such as described in "Comprehensive Handbook of Hydrosilylation," B. Marciniec (ed), Pergamon Press, New York (1992), the entire contents of which are incorporated by reference herein.

Some specific examples of useful hydridoalkoxysilanes (15) include hydridotrimethoxysilane, hydridotriethoxysilane, hydridomethyldimethoxysilane, hydridomethyldiethoxysilane, hydridodimethylmethoxysilane, hydridodimethylethoxysilane, and the like.

Among the epoxysilanes that can be prepared in accordance with Synthesis Process 4 are:

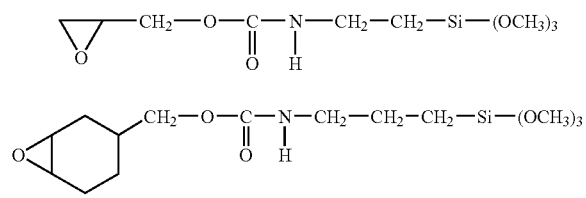

Synthetic Process 5: Reaction of Halocarbylsilane with Cyanate in the Presence of Ethylenically Unsaturated Alcohol to Provide Ethylenically Unsaturated Alkoxysilane Intermediate which is then Subjected to Epoxidation to Provide Epoxysilane Halocarbylsilane is reacted in a first step with cyanate in the presence of an alcohol possessing terminal ethylenic unsaturation in a first step, advantageously in the presence of a suitable catalyst and/or inert solvent, to provide ethylenically unsaturated hydrolyzable silane intermediate possessing at least one urethane linkage, the intermediate then being subjected in a second step to any known or conventional epoxidation procedure, including the use of peracids as described in, e.g., "Modern Synthetic Reactions", Second Edition, H. O. House (ed), W. A. Benjamin, Inc. Menlo Park (1972), and transition metal catalyzed epoxidations as described in, e.g., K. A. Jorgensen, "Chemical Reviews", 89(3), 431 (1989), the entire contents of both of which are incorporated by reference herein, to provide the corresponding epoxysilane.

Step 1: Reaction of Halocarbylsilane with Cyanate and Ethylenically Unsaturated Alcohol to Provide Ethylenically Unsaturated Alkoxysilane In one embodiment, the halocarbylsilane is one of general Formula (15):

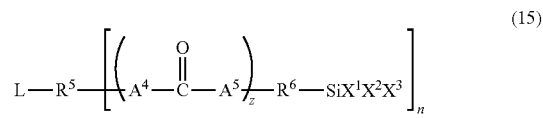

wherein $R^5$, $R^6$, $A^4$, $A^5$, $X^1$, $X^2$ and $X^3$ and a have the aforestated meanings, L is Cl, Br or I, z is 0 and n is 1 to 6 and preferably 1 or 2.

Useful halocarbylsilanes (15) include 3-chloropropyltrimethoxysilane, 3-chloropropyltriethoxysilane, 3-bromopropyltrimethoxysilane, 4-chlorobutyldimethylethoxysilane, 3-chloropropyltriethoxysilane, 3-chloropropylmethyldimethoxysilane, 4-chlorobutylphenylmethyl-n-propoxysilane, 3-iodopropyltrimethoxysilane, 4-(2-chloroethyl)-1,7-bis-(trimethoxysilyl)heptane, and the like.

Useful cyanate reactants include those of general formula (16):

wherein M is a metal, ammonium or phosphonium group and w is the valence of M, specifically of from 1 to 4, more specifically 1 or 2 and most specifically 1.

Cyanates (16) which can be employed in the first step of Synthetic Process 5 include those in which M is lithium, sodium, potassium, calcium, magnesium, ammonium or phosphonium. Preferred cyanates are sodium cyanate and potassium cyanate.

Alcohols possessing terminal ethylenic unsaturation can be any of those of general Formula (17):

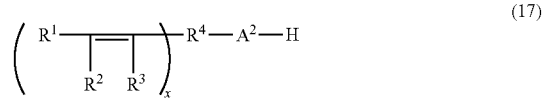

wherein $R^1$, $R^2$, $R^3$ and $R^4$ have the aforestated meanings, x is 1 to 6 and $A^2$ is oxygen.

Suitable ethylenically unsaturated alcohols include allyl alcohol, methallyl

alcohol, 3-buten-1-ol, 8-octen-1-ol, 3-methyl-3-buten-1-ol, 4-vinylphenol, 4-vinylbenzyl alcohol, 3-hydroxy-1,4-pentadiene and the like.

The first step reaction of halohydrocarbylsilane (15), cyanate (16) and ethylenically unsaturated alcohol (17) to provide ethylenically unsaturated alkoxysilane intermediate (14) can be regarded as proceeding in accordance with the following Equation (18):

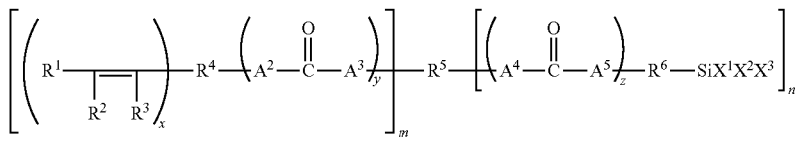

Halocarbylsilane (15)+Cyanate (16)+Ethylenically
Unsaturated Alcohol (17)→ (18)

wherein $R^1$, $R^2$, $R^3$, $R^4$, $R^5$, $R^6$, $A^4$, $A^5$, M, L and w have the aforestated meanings, $A^2$ is oxygen, $A^3$ is —NH—, x is 1 to 6, y is 1, z is 0, m is 1 to 6 and n is 1 to 6.

Step 2: Epoxidation of Ethylenically Unsaturated Alkoxysilane Intermediate to Provide Epoxysilane The ethylenically unsaturated alkoxysilane intermediate obtained in the first step of Synthetic Process 5 is epoxidized under known and conventional epoxidation conditions to provide epoxysilane in accordance with the invention. Thus, e.g., epoxidation of ethylenically unsaturated alkoxysilane from Equation (18) with a peracid such as peracetic acid, perbenzoic acid, m-chloroperbenzoic acid, or transition metal catalysts such as molybdenum IV peroxo compounds, vanadium complexes, tetra-isoproproxytitanate-tartrate complex in presence of t-butylhydroperoxide, at temperatures from 0° to about 100° C., and at reduced, atmospheric or high pressure, in the absence or presence of organic solvents such as methylene choride, chloroform, hexanes, ethyl acetate, and the like, and under anhydrous conditions, provides epoxysilane of general formula (1):

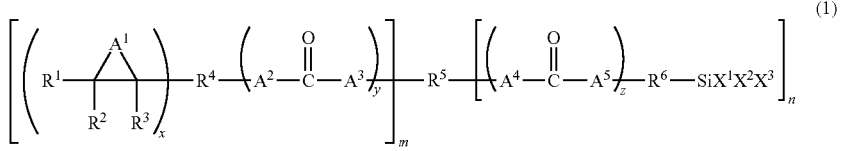
(1)

wherein $R^1$, $R^2$, $R^3$, $R^4$, $R^5$, $R^6$, $A^4$ and $A^5$ have the afore stated meanings, $A^1$ and $A^2$ are oxygen, $A^3$ is —NH—, x is 1 to 6, y is 1, z is 0, m is 1 to 6 and n is 1 to 6.

The epoxysilanes of this invention are useful for a variety of applications including those hereinafter described.

In one embodiment herein, there is provided a curable composition for treating or coating a substrate comprising at least one epoxysilane in accordance with the invention.

The epoxysilane(s) incorporated in the aforementioned curable composition can range in solubility in water from being fully miscible therein to being soluble e.g., up to about 600 grams per liter (g/l), preferably up to about 400 g/l and more specifically up to about 300 g/l.

The substrate can be any organic or inorganic material such as fibers, particulates and sheet-like structures and can be composed of inorganic minerals, silicates, silica, clays, ceramics, carbon, organic polymers, diatomaceous earth, sol-gel, metals and combinations thereof.

In one specific embodiment herein, the substrate can be a mineral filler provided, e.g., as discrete particles or group of particles in the form of aggregates or agglomerates. Mineral fillers can be mixed with other fillers that do not react with the epoxysilane of this invention. These fillers can be used to either extend the epoxysilane and/or polymers used to form a composite, coating, adhesive, sealant, rubber, and the like, or to reinforce the epoxysilane or polymers used to make these compositions. Some representative non-limiting examples of suitable mineral fillers include one or metal oxides such as silica (pyrogenic and/or precipitated), titanium dioxide, aluminosilicate, alumina and siliceous materials including clays, talc, used alone or in combination with one or more other fillers, e.g., mixture of silica and carbon black. In another embodiment, alumina can be used either alone or in combination with silica. In a further specific embodiment, the filler(s) can be hydrated or in anhydrous form. The use of alumina in rubber compositions is known; see, for example, U.S. Pat. No. 5,116,886 and EP 631 982, the entire contents of both of which are incorporated by reference herein.

In another embodiment, an epoxysilane of the invention is applied to a filler which functions as a carrier, e.g., a porous or high surface area filler or organic polymer having sorptive capacity, e.g., on capable of carrying up to about 75 weight percent epoxy silane while maintaining its free-flowing properties. Sorptive filler will be essentially inert to the epoxysilane and capable of releasing epoxysilane therefrom when added to a polymeric composite or elastomeric composition. The sorptive capacity of these porous fillers is typically determined by measuring the quantity of epoxysilane extracted with an organic solvent under certain specified conditions. A suitable extraction procedure is described in U.S. Pat. No. 6,005,027, the entire contents of which are incorporated herein by reference. Suitable filler-carriers include, but are not limited to, porous organic polymers, carbon black, diatomaceous earth and silicas that are characterized by a relatively low differential of less than 1.3 between the infrared absorbance at 3502 $cm^{-2}$ of the silica when taken at 105° C. and when taken at 500° C. as described in U.S. Pat. No. 6,005,027. In one embodiment, the amount of epoxysilane that can be loaded on the carrier is from about 0.1 to about 70 weight percent and in another embodiment, from about 10 to about 50 weight percent.

Other suitable mineral fillers include those in which the epoxysilane is reactive with the surface of the filler. Fillers of this type include particulate precipitated silica, clays, siliceous minerals, glass, mica, and the like. The surfaces of these fillers are reactive with epoxysilane, particularly when the fillers have reactive surface silanols. The surface-reactive mineral fillers herein can be provided in a hydrated form. Mixtures of surface-reactive mineral fillers can be utilized, e.g., those possessing metal hydroxyl surface functionality such as alumina and other metal oxides, in combination with those possessing such as silica, silicates, etc.

Combinations of two or more of the general types of fillers can be used herein, e.g., two or more fillers of the essentially inert type, the sorptive type and the surface-reactive type.

Metal substrates include any metal that has or has not been treated with chromate, zinc, tin or any rust-inhibiting or preventing substance. Some non-limiting examples of metals are those selected from the group consisting of surface cold-rolled steel; galvanized steel; hot dip galvanized steel; prime steel; aluminum; steel coated with at least one metal chosen from the non-limiting group consisting of zinc, zinc alloy, aluminum and aluminum alloy, aluminum, aluminum alloy, copper, brass, and iron; and combinations thereof. In another specific embodiment herein, the metal substrate is provided in the form of a sheet, a bar, a rod, a wire, a foil and combinations thereof.

The metal substrate is coated with the composition containing epoxysilane herein, the composition is cured thereon and, optionally, a different coating, is applied to the cured composition. Applying the composition of this invention to the desired substrate can be accomplished by such known and conventional procedures as roll-coating, specifically, reverse roll coating; dip-coating, flood coating, spray and drawdown techniques, and the like.

The epoxysilane-coating composition of the invention can be formulated as, e.g., a paint, such as a polyester-based paint, a rubber, an adhesive, etc.

The curable compositions of the invention also include adhesion-promoting compositions comprising one or more solvents such as water, an alcohol, ester, ketone, hydrocarbon, ether, and the like, one or more wetting agents, organic resin film formers, such as an epoxy resin or urethane resin, and other hydrolyzable organosilane compounds such as vinyltrimethoxysilane, vinylmethyldiethoxysilane, methacryloxypropyltrimethoxysilane, methyltripropylsilane, and the like. The adhesion promoting composition can contain as its adhesion promoting component an epoxysilane herein in an amount, e.g., of from about 0.1 to about 90 weight percent, preferably from about 0.5 to about 15 weight percent and more preferably from about 0.75 to about 5 weight percent, said weight percents being based on the total weight of the adhesion promoting composition.

In another specific embodiment, the curable composition herein can comprise a mineral material sizing agent containing one or more of water, solvents, organic film forming polymers such as urethanes, epoxys, polyesters, polyolefins, polyethers, and the like, wetting agents, antistatic agents and other hydrolyzable organosilane compounds. In a particular embodiment, a mineral material sizing agent composition can comprise epoxysilane of the invention in an amount, e.g., of from about 0.05 to about 25 weight percent, preferably from about 0.1 to about 10 weight percent and more preferably from about 0.5 to about 5 weight percent, said weight percents being based on the total weight of the mineral material sizing agent composition.

In yet another embodiment of curable composition herein, the composition can be a coupling agent containing at least one of water, organic solvents, organic film forming polymers such as urethanes, epoxys, polyesters, polyolefins, polyethers, and the like, wetting agents, antistatic agents, and other hydrolyzable organosilane compounds. The coupling agent composition can contain epoxysilane of the invention in an amount, e.g., from about 0.05 to about 25 weight percent, preferably from about 0.1 to about 10 weight percent and more preferably from about 0.5 to about 5 weight percent, said weight percent being based on the total weight of the coupling agent composition.

The curable composition of the invention can also be formulated as a conversion coating composition containing at least one of solvent such as water, an alcohol, ether, ester, ketone, and the like, wetting agents, metal oxides such as cerium oxide, surfactant, catalyst and acid. In a particular embodiment, the conversion coating composition can contain epoxysilane of this invention in an amount, e.g., from about 0.01 to about 50 weight percent, preferably from about 0.1 to about 30 weight percent, and more preferably from about 0.5 to about 16 weight percent, said weight percents being based on total weight of the conversion coating composition.

The composition of the invention can be provided as a sol-gel composition further containing at least one of solvent such as water, alcohol, ester, ether, ketone, and the like, and a colloid consisting of a metal or metalloid surrounded with ligands such as oxide, alkyl, alkoxide, carboxylic acid, ketone ester, and the like. The sol-gel composition can incorporate epoxysilane herein in an amount, e.g., of from about 0.01 to about 50 weight percent, preferably from about 0.1 to about 30 weight percent, and more preferably from about 0.5 to about 20 weight percent, said weight percents being based on the total weight of the sol-gel composition.

The curable composition of the invention can be formulated as a sealant composition containing at least one of filler, plasticizer, organic polymer solvent, antioxidant, UV light stabilizer, thixotropic agent, surfactant, catalyst, and the like. In a particular embodiment, the sealant composition can contain the epoxysilane of the invention, e.g., in an amount of from about 0.1 to about 10 weight percent, preferably from about 0.5 to about 5 weight percent and more preferably from about 5 weight percent, said weight percents being based on the total weight of the sealant composition.

The epoxysilane-containing curable composition of the invention can contain water of any purity, e.g., distilled water and/or nano-pure water. The amount of water can vary greatly depending on the amount and/or type of epoxysilane herein as well as the amount and/or type of any additional component present in the composition such as surfactant; catalyst, cosolvent, organic acid, and the like. The amount of water can also vary based upon the desired surface tension of the aqueous solution of epoxysilane, the desired pH of the aqueous solution, the desired stability of the aqueous solution and the desired level of hydrolysis of its epoxysilane component. In one embodiment, the amount of water is greater than the amount of epoxysilane component(s). In another embodiment, the amount of water can range, e.g., from about 50 to about 99.9 weight percent, preferably from about 75 to about 99 weight percent, and more preferably from about 85 to about 98 weight percent, said weight percents being based on the total weight of the epoxysilane composition.

The epoxysilane composition of the invention can further comprise at least one surfactant such a polyoxyethylene alkyl ether, polyoxyethylene alkyl phenylether, polyoxyethylene fatty acid ester, sorbitan fatty acid ester, polyoxyethylene sorbitan fatty acid ester fatty acid salt, alkyl sulfate ester salt, alkyl benzene sulfonate, alkyl phosphate, alkylallyl sulfate ester salt, polyoxyethylene alkylphosphate ester, quaternary ammonium salt, long chain alkyl trimethylammonium salt, long chain alkyl benzyl dimethyl ammonium salt, di(long chain alkyl) dimethyl ammonium salt, ethoxylated nonyl phenol, polyvinyl alcohol, etc., and combinations thereof. Particular embodiments include, e.g., Triton X-100. (Dow Chemical Company) and Silwet* L-77 (Momentive Performance Materials Inc.). The amount of these and other surfactants can vary considerably depending on the amount and/or type of epoxysilane herein, the amount and/or type of water as well as the amount and/or type of any additional component in the composition present such as catalyst, cosolvent and organic acid. The amount of surfactant can also vary based upon the desired surface tension of an aqueous solution, the desired pH of the solution, the desired stability of the solution and the desired level of hydrolysis of the epoxysilane. In one embodiment herein, the amount of surfactant is less than the amount of the epoxysilane. In another specific embodiment, the amount of surfactant can range, e.g., from about 0.0001 to about 5 weight percent, preferably from about 0.001 to about 2 weight percent and more preferably from about 0.02 to about 0.2 weight percent, said weight percents being based on the total weight of the epoxysilane composition.

Solvent may serve as a diluent, carrier, stabilizer, refluxing aid or heating agent in any of the curable compositions of the invention. Generally, any inert solvent, i.e., one which does not enter into the reaction or adversely affect curing of the compositions, can be used. In one embodiment, solvents are those which are liquid under normal conditions and have boiling points below about 150° C. Some non-limiting examples of useful solvents include aromatics, hydrocarbons, ethers, aprotic solvents and chlorinated hydrocarbon solvents such as toluene, xylene, hexane, butane, diethyl ether, dimethylformamide, dimethyl sulfoxide, carbon tetrachloride, methylene chloride, etc., and their combinations.

The stability of aqueous compositions containing the epoxysilane of the invention may be increased by the addition of one or more solvents thereto. The solvent can be an organic such as alcohol (e.g., butyl alcohol), glycol (e.g., propylene glycol), ester, etc., and combinations thereof. The amount of solvent can vary within wide limits depending on the amount and/or type of epoxysilane employed, the amount and/or type of water as well as the amount and/or type of any additional component(s) such as surfactant, catalyst, organic acid, etc. The amount of any cosolvent can also vary considerably based upon the desired surface tension of the aqueous solution, the desired pH of the aqueous solution, the desired stability of the aqueous solution and the desired level of hydrolysis of the incorporated epoxysilane. In a specific embodiment herein, as the epoxysilane of the invention undergoes hydrolysis an amount of alcohol may be produced which may be sufficient to form an aqueous-stable epoxysilane composition without the addition of cosolvent. The amount of such alcohol can range from about 0.1 to about 50 weight percent, advantageously from about 0.1 to about 20 weight percent, and still more advantageously from about 0.2 to about 6 weight percent, of the total weight of the epoxysilane-containing composition.

It can be advantageous to maintain the pH of a curable composition herein so as to minimize the rate of hydrolysis and subsequent condensation of its epoxysilane component and maximize its stability in aqueous media. By controlling pH, an aqueous-based epoxysilane composition in accordance with the invention can possess an aqueous stability of at least about 3 months, preferably at least about 4 months, more preferably at least about 5 months and most preferably at least about 6 months. Improvement or optimization of the aqueous stability of the composition can generally be accomplished by adjusting the pH to within a range of from about 2 to about 9, preferably from about 3 to about 8, more preferably from about 3 to about 7 and most preferably from about 3.5 to about 6.0. Minimization of the extent of hydrolysis of the epoxysilane herein can be accomplished through the use of an organic acid such as acetic acid, formic acid, citric acid, phosphoric acid, etc., and combinations thereof. It will be understood herein that the amount of organic acid used can vary considerably depending on the amount and/or type of epoxysilane incorporated in the composition, the amount and/or type of water and the amount and/or type of any additional component(s) such as surfactant, catalyst and solvent. The amount of organic acid can also vary based upon the desired surface tension of the composition, the desired pH of the composition, the desired stability of the composition and the desired level of hydrolysis of its epoxysilane component. In general, the amount of organic acid used for adjusting the pH of a curable composition herein can range from about 0.001 to about 2.0 weight percent, preferably from about 0.01 to about 1.0 weight percent and more preferably from about 0.11 to about 0.2 weight percent, said weight percents being based on the total weight of the composition.

Curable compositions in accordance with the invention may also contain one or more catalysts examples of which include tin catalysts such dibutyltin dilaurate, dibutyltin diacetate, dibutylytin maleate, dilauryltin diacetate, dioctyltin diacetate, dibutyltin-bis(4-methylaminobenzoate), dibuyltin-dilauryl mercaptide, dibutyltin-bis(6-methylaminocaproate) and combinations thereof. The amount of catalyst can vary within wide limits depending on the amount and/or type of epoxysilane present in the composition as well as the amount and/or type of water and/or other component(s) such as surfactant, solvent and organic acid, etc., incorporated therein. The amount of catalyst can also vary based upon the desired surface tension of the composition, the desired pH of the composition, the desired aqueous stability of the composition and the desired level of hydrolysis of its epoxysilane component. For example, the amount of catalyst can range from about 0.001 to about 1.0 weight percent, preferably from about 0.001 to about 0.5 weight percent and more preferably from about 0.01 to about 0.2 weight percent, said weight percents being based on the total weight of the epoxysilane-containing composition.

The following examples are further illustrative of the invention.

Example 1

This example illustrates the preparation of 3-trimethoxysilylpropyl-carbamic acid oxiranylmethyl ester which has the structure:

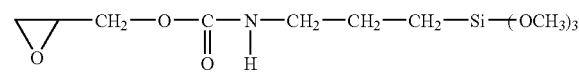

Glycidol (7.4 grams, 100 millimoles (mmol)) was slowly added to a mixture of gamma-isocyanatopropyltrimethoxysilane (107 mmol) and dibutyltin dilaurate (0.0295 grams) under stirring. The temperature of the mixture was raised to 53° C. over 25 minutes while stirring was continued. The reaction mixture was then stirred at ambient temperature for two hours. Infrared testing then indicated the absence of an NCO peak at 2300 cm$^{-1}$. The reaction was then deemed completed. $^{13}$C NMR testing confirmed the identity of the desired product.

Example 2

This example illustrates the preparation of 3-triethoxysilylpropyl-carbamic acid oxiranyl methyl ester which has the structure:

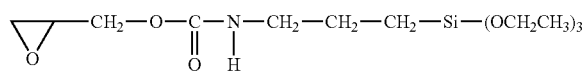

Glycidol (7.4 grams, 100 mmol) was slowly added to a mixture of gamma-isocyanatopropyltriethoxysilane (100 mmol) and dibutyltin dilaurate (0.0395 grams) under stirring. The reaction mixture was then stirred at ambient temperature for two hours. Infrared testing then indicated the absence of an NCO peak at 2300 cm$^{-1}$. The reaction was then deemed completed. $^{13}$C NMR testing confirmed the identity of the desired product.

Example 3

A 2% weight treatment solution of the 3-trimethoxysilyl-propylcarbamic acid oxiranylmethyl ester of Example 1 was prepared as follows: non-ionic surfactant (Triton X-100)—50 mg, silane—1 g, distilled water—48.95 g were mixed together. Test panels were unpolished cold rolled steel cut, 4"×6"×0.032" from ACT Laboratories, The panels were degreased with standard alkaline cleaner (65° C. for 2 minutes), rinsed with distilled water and then dried with compressed nitrogen. A 4"×6"×0.032" control panel treated with an immersion zinc phosphate conversion coating (Henkel Bonderite 958) followed by Parcolene 60 rinse was gotten from ACT Laboratories. Panels A and B were coated with the treatment composition and the coatings were cured at 120° C. for 20 minutes prior to being painted. The paint, a primerless polyester-based system from Sherwin Williams, was applied by drawdown technique. The dry film thickness was approximately 1.2 mil. The baking conditions were 15 minutes at 175° C. Creepage data, measured per test process ASTM D1654, are recorded as minimum, maximum and average distance from the scribe in millimeters and are presented in the table below.

TABLE

Results of Creepage Tests

| Panel Coating | Creepage, mm | | |
|---|---|---|---|
| | Average | Minimum | Maximum |
| Example 1 (MeO)$_3$Si(CH$_2$)$_3$NHCOOCH$_2$(CHOCH$_2$) (Panel A) | 2.4 | 1.5 | 3.3 |
| Example 2 (MeO)$_3$Si(CH$_2$)$_3$NHCOOCH$_2$(CHOCH$_2$) (Panel B) | 2.1 | 0.8 | 3.3 |
| Chromium-sealed zinc phosphate (Control Panel) | 2.2 | 1.5 | 3.0 |

Panels A and B show comparable creepage performance compared to the chromium-sealed zinc phosphate cold rolled steel control. Creepage is an indicator of the ability of the pretreatment to improve the adhesion of paint and in some cases to retard corrosion reactions, thereby protecting the underlying metal from corrosion. The lower the measured creepage, the better the overall system (conversion coating plus paint) is at protecting the metal. If the same paint is used for the studies, a ranking of the effectiveness of the pretreatment with the particular paint and substrate is gotten.

While the invention has been described in detail in connection with specific embodiments thereof, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Accordingly, the invention is not limited by the foregoing description.

The invention claimed is:
1. An epoxysilane which contains at least one epoxy group, at least one hydrolyzable silyl group and one or more linkages containing a carbonyl group bonded to heteroatoms selected from the group consisting of oxygen, sulfur and nitrogen with at least one such heteroatom being nitrogen, there being no such linkage in which both an epoxy group and hydrolyzable silyl group are directly or indirectly bonded to the same nitrogen heteroatom in the linkage, the epoxysilane having the general Formula (I):

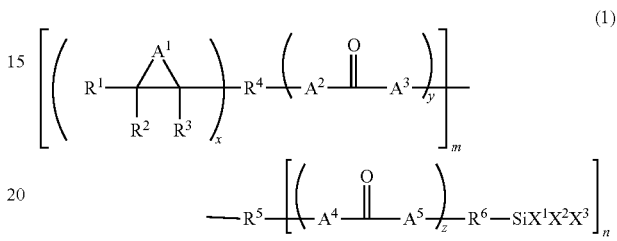

(1)
wherein:
each occurrence of $R^1$ is independently hydrogen or an alkyl group containing from 1 to 6 carbon atoms;
each occurrence of $R^2$ is independently hydrogen or a hydrocarbyl group containing from 1 to 12 carbon atoms and selected from the group consisting of monovalent alkyl, alkenyl, arenyl, aryl and aralkyl groups and divalent alkylene, alkenylene, arenylene, arylene and aralkylene groups in which one carbon atom of $R^2$ is covalently bonded to a carbon of the epoxy ring and the same or different carbon atom of $R^2$ is covalently bonded to a carbon atom of $R^3$ or $R^4$ to form a cyclic aliphatic structure;
each occurrence of $R^3$ is independently hydrogen or a hydrocarbyl group containing from 1 to 12 carbon atoms and selected from the group consisting of monovalent alkyl, alkenyl, arenyl, aryl and aralkyl groups and divalent alkylene, alkenylene, arenylene, arylene and aralkylene groups in which one carbon atom of $R^3$ is covalently bonded to a carbon atom of the epoxy ring and the same or different carbon atom of $R^3$ is covalently bonded to a carbon atom of $R^2$ or $R^4$ to form a cyclic aliphatic structure;
each occurrence of $R^4$ is independently a divalent or polyvalent hydrocarbyl group containing up to 12 carbon atoms and selected from the group consisting of divalent alkylene group and polyvalent hydrocarbyl group in which one carbon atom of $R^4$ forms a covalent bond with the carbon atom of the epoxy ring, the same or different carbon atom of $R^4$ forms a bond with a nitrogen, oxygen or sulfur heteroatom bonded to a carbonyl group, and the same or different carbon atom of $R^4$ forms at least one covalent bond with a carbon atom of $R^2$ or $R^3$;
each occurrence of $R^5$ is independently a divalent or polyvalent hydrocarbyl group containing up to 24 carbon atoms derived by substitution of at least one hydrogen on an alkyl, alkenyl, arenyl, aryl or aralkyl group and, optionally, at least one oxygen or sulfur atom; or a divalent or polyvalent organic polymer group;
each occurrence of $R^6$ is a divalent alkylene, alkenylene, arenylene, arylene or aralkylene group containing up to 12 carbon atoms and, optionally, at least one oxygen or sulfur atom;

each occurrence of $X^1$ is independently selected from the group consisting of $R^7O$—, $R^7C(=O)O$—, $R^7{}_2C=NO$— and $R^7{}_2NO$— wherein each $R^7$ is independently selected from the group consisting of hydrogen or alkyl, alkenyl, arenyl, aryl and aralkyl groups wherein each $R^7$, other than hydrogen, independently contains from 1 to 18 carbon atoms and, optionally, at least one oxygen or sulfur atom;

each occurrence of $X^2$ and $X^3$ is independently selected from the group consisting of $R^8$, $R^{8O}$—, $R^8C(=O)O$—, $R^8{}_2C=NO$— and $R^8{}_2NO$— wherein each $R^8$ is independently selected from the group consisting of hydrogen or alkyl, alkenyl, arenyl, aryl and aralkyl groups wherein each $R^8$, other than hydrogen, contains from 1 to 18 carbon atoms and, optionally, at least one oxygen or sulfur atom;

each occurrence of $A^1$ is independently selected from divalent oxygen (—O—) or sulfur (—S—);

each occurrence of $A^2$ is independently selected from divalent oxygen (—O—), sulfur (—S—) or substituted nitrogen of the structure —$NR^9$— wherein $R^9$ is independently hydrogen or alkyl, alkenyl, arenyl, aryl, aralkyl or —$R^6$—$SiX^1X^2X^3$ group wherein each $R^9$, other than hydrogen, independently contains from 1 to 18 carbon atoms, and with the proviso that when $A^2$ is oxygen or sulfur, then $A^3$, infra, is —$NR^{10}$—;

each occurrence of $A^3$ is independently selected from divalent oxygen (—O—), sulfur (—S—) or substituted nitrogen of the structure —$NR^{10}$— wherein each $R^{10}$ is independently hydrogen or hydrogen, independently contains from 1 to 18 carbon atoms, and with the proviso that when $A^3$ is oxygen or sulfur, then $A^2$ is —$NR^9$—;

each occurrence of $A^4$ is independently selected from divalent oxygen (—O—), sulfur (—S—) or substituted nitrogen of the structure —$NR^{11}$— wherein each $R^{11}$ is independently hydrogen or alkyl, alkenyl, arenyl, aryl, aralkyl or —$R^6$—$SiX^1X^2X^3$ group wherein each $R^{11}$, other than hydrogen, independently contains from 1 to 18 carbon atoms, and with the proviso that when $A^4$ is oxygen or sulfur, then $A^5$, infra, is —$NR^{12}$—;

each occurrence of $A^5$ is independently selected from divalent oxygen (—O—), sulfur (—S—) or substituted nitrogen of the structure —$NR^{12}$— wherein $R^{12}$ is hydrogen or alkyl, alkenyl, arenyl, aryl, aralkyl or —$R^6$—$SiX^1X^2X^3$ group wherein each $R^{12}$, other than hydrogen, independently contains from 1 to 18 carbon atoms, and with the proviso that when $A^2$ is oxygen or sulfur, then $A^4$ is —$NR^{11}$—; and, each occurrence of subscripts m, n, x, y and z independently is an integer wherein m is 1 to 6; n is 1 to 6; x is 1 to 6; y is 0 or 1; and, z is 0 or 1, with the proviso that y+z is equal to or greater than 1.

2. The epoxysilane of claim 1 wherein $A^4$ is oxygen or sulfur, $A^5$ is —NH—, m is 1, x is 1 to 6, y is 0 and z is 1.

3. The epoxysilane of claim 2 wherein $R^5$ is a divalent or polyvalent hydrocarbyl group containing up to 24 carbon atoms derived by substitution of at least one hydrogen on an alkyl, alkenyl, arenyl, aryl or aralkyl group and, optionally, at least one oxygen or sulfur atom.

4. The epoxysilane of claim 1 wherein $A^2$ is oxygen or sulfur, each of $A^3$ and $A^4$ is —NH—, $A^5$ is sulfur or —$NR^{12}$— wherein $R^{12}$ is alkyl, alkenyl, arenyl, aryl, aralkyl or —$R^6$—$SiX^1X^2X^3$ group containing 1 to 18 carbon atoms, x is 1 to 6, y is 1, z is 1, m is 1 to 6 and n is 1 to 6.

5. The epoxysilane of claim 1 wherein $A^1$ and $A^2$ are oxygen, $A^3$ is —NH—, x is 1 to 6, y is 1, z is 0, m is 1 to 6 and n is 1 to 6.

6. The epoxysilane of claim 2 wherein $R^1$, $R^2$ and $R^3$ each is hydrogen, $R^4$, $R^5$ and $R^6$ each is the same or different divalent hydrocarbyl group, $A^1$ and $A^4$ are oxygen, $X^1$ is —$OR^7$ wherein $R^7$ is alkyl, $X^2$ and $X^3$ each is independently $R^8$ or —$OR^8$ wherein $R^8$ is alkyl, x is 1 and n is 1.

7. The epoxysilane of claim 6 wherein $R^4$, $R^5$ and $R^6$ each is the same or different alkylene group and $R^7$ and $R^8$ are independently methyl or ethyl.

8. The epoxysilane of claim 7 wherein $X^2$ and $X^3$ each is the same or different —$OR^8$ group.

9. The epoxysilane of claim 4 wherein $R^1$, $R^2$ and $R^3$ each is hydrogen, $R^4$, $R^5$ and $R^6$ each is the same or different divalent hydrocarbyl group, $A^1$ and $A^2$ are oxygen, $X^1$ is —$OR^7$ wherein $R^7$ is alkyl and $X^2$ and $X^3$ each is independently $R^8$ or —$OR^8$ wherein $R^8$ is alkyl, x is 1, m is 1 and n is 1.

10. An epoxysilane which contains at least one epoxy group, at least one hydrolyzable silyl group and one or more linkages containing a carbonyl group bonded to heteroatoms selected from the group consisting of oxygen, sulfur and nitrogen with at least one such heteroatom being nitrogen, there being no such linkage in which both an epoxy group and hydrolyzable silyl group are directly or indirectly bonded to the same nitrogen heteroatom in the linkage, the epoxysilane having general Formula (1)

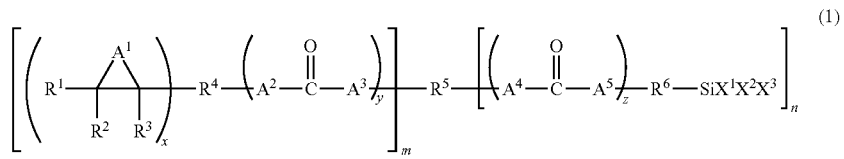

wherein:
each occurrence of $R^1$ is hydrogen;
each occurrence of $R^2$ is hydrogen;
each occurrence of $R^3$ is hydrogen;
each occurrence of $R^4$ is a divalent alkylene group containing up to 12 carbon atoms;
each occurrence of $R^5$ is a divalent alkylene group containing up to 24 carbon atoms;
each occurrence of $R^6$ is a divalent alkylene group containing up to 12 carbon atoms;
each occurrence of $X^1$ is —$OR^7$, wherein each occurrence of $R^7$ is independently methyl or ethyl;
each occurrence of $X^2$ and $X^3$ is independently $R^8$ or —$OR^8$, wherein each occurrence of $R^8$ is independently methyl or ethyl;
each occurrence of $A^1$ is oxygen (—O—);
each occurrence of $A^2$ is oxygen (—O—);
each occurrence of $A^3$ is —NH—:
each occurrence of $A^4$ is —NH—:
each occurrence of $A^5$ is independently selected from sulfur (—S—) or substituted nitrogen of the structure —$NR^{12}$— wherein $R^{12}$ is alkyl, alkenyl, arenyl, aryl, aralkyl or —R⁶—SiX¹X²X³ group wherein each R¹² independently contains from 1 to 18 carbon atoms; and,
each occurrence of subscripts m, n, x, y and z independently is an integer wherein m is 1; n is 1; x is 1; y is 1; and, z is 1, with the proviso that y+z is equal to or greater than 1.

11. The expoxysilane of claim 10 wherein X² and X³ each is the same or different —OR⁸ group.

12. The epoxysilane of claim 5 wherein R¹, R² and R³ each is hydrogen, R⁴, R⁵ and R⁶ each is the same or different divalent hydrocarbyl group, X¹ is —OR⁷ wherein R⁷ is alkyl, X² and X³ each is independently R⁸ or —OR⁸ wherein R⁸ is alkyl, x is 1, m is 1 and n is 1.

13. An epoxysilane which contains at least one epoxy group, at least one hydrolyzable silyl group and one or more linkages containing a carbonyl group bonded to heteroatoms selected from the group consisting of oxygen, sulfur and nitrogen with at least one such heteroatom being nitrogen, there being no such linkage in which both an epoxy group and hydrolyzable silyl group are directly or indirectly bonded to the same nitrogen heteroatom in the linkage, the epoxysilane having general Formula (1)

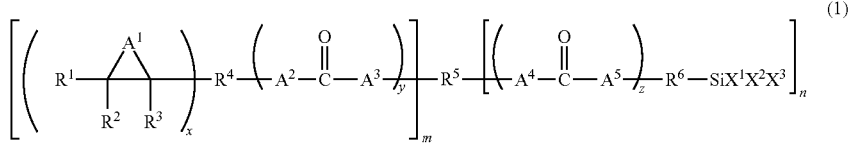

wherein:
each occurrence of R¹ is hydrogen:
each occurrence of R² is hydrogen;
each occurrence of R³ is hydrogen;
each occurrence of R⁴ is a divalent alkylene group containing up to 12 carbon atoms;
each occurrence of R⁵ is a divalent alkylene group containing up to 24 carbon atoms;
each occurrence of R⁶ is a divalent alkylene group containing up to 12 carbon atoms;
each occurrence of X¹ is —OR⁷, wherein each occurrence of R⁷ is independently methyl or ethyl;
each occurrence of X² and X³ is independently R⁸ or —OR⁸, wherein each occurrence of R⁸ is independently methyl or ethyl;
each occurrence of A¹ is oxygen (—O—);
each occurrence of A² is oxygen (—O—);
each occurrence of A³ is —NH—;
each occurrence of A⁴ is independently selected from divalent oxygen (—O—), sulfur (—S—) or substituted nitrogen of the structure —NR¹¹— wherein each R¹¹ is independently hydrogen or alkyl, alkenyl, arenyl, aryl, aralkyl or —R⁶—SiX¹X²X³ group wherein each R¹¹, other than hydrogen, independently contains from 1 to 18 carbon atoms, and with the proviso that when A⁴ is oxygen or sulfur, then A⁵, infra, is —NR¹²—:
each occurrence of A⁵ is independently selected from divalent oxygen (—O—), sulfur (—S—) or substituted nitrogen of the structure —NR¹²— wherein R¹² is hydrogen or alkyl, alkenyl, arenyl, aryl, aralkyl or —R⁶—SiX¹X²X³ group wherein each R¹², other than hydrogen, independently contains from 1 to 18 carbon atoms, and with the proviso that when A² is oxygen or sulfur, then A⁴ is —NR¹¹—; and, each occurrence of subscripts m, n, x, y and z independently is an integer wherein m is 1; n is 1; x is 1; y is 1; and, z is 0.

14. The epoxysilane of claim 13 wherein X² and X³ each is the same or different —OR⁸ group.

15. An epoxysilane selected from the group consisting of N-(3-trimethoxysilylpropyl)carbamic acid oxiranyl methyl ester; 3-triethoxysilylpropyl-carbamic acid oxiranyl methylester; [3-(triethoxysilyl)propyl]-carbamic acid oxiranyl nonadecyl ester; [3-(triethoxysilyl)propyl]-carbamic acid 2-[2-(2-methoxyethoxy)ethoxy]oxiranyl ethyl ester; carbonic acid 1,1-dimethylethyl 3-[[[[3-(triethoxysilyl)propyl]amino]carbonyl]oxy]oxiranyl phenyl ester; [3-(triethoxysilyl)propyl]-carbamic acid oxiranyl-3-phenyl-2-propenyl ester; [3-(triethoxysilyl)propyl]-carbamic acid oxiranyl-3,3-diphenyl-3H-naphtho[2,1-b]pyran-9-yl ester; [3-(ethoxy-dimethoxysilyl)propyl]-carbamic acid oxiranyl methyl ester; [3-(diethoxymethoxysilyl)propyl]-carbamic acid oxiranyl methyl ester; [3-(triethoxysilyl)propyl]-carbamic acid oxiranyl-3,3,4,4,5,5,6,6,7,7,8,8,8-tridecafluorooctyl ester; [3-(triethoxysilyl)propyl]-carbamic acid oxiranyl-1,3,5-benzenetriyltris(methylene)ester; [3-(triethoxysilyl)propyl]-carbamic acid oxiranyl-1,3,5-benzenetriyltris(methylene) ester; [3-(triethoxysilyl)propyl]-carbamic acid oxiranyl-phenylmethyl ester; [3-(trimethoxysilyl)propyl]-carbamic acid oxiranyl ethyl ester; [3-(trimethoxysilyl)propyl]-carbamic acid oxiranyl-1,1-dimethylethyl ester; [3-(triethoxysilyl)propyl]-carbamic acid oxiranyl-1,1-dimethylethyl ester; [3-(trimethoxysilyl)propyl]-carbamic acid oxiranyl methyl ester; [3-(triethoxysilyl)propyl]-carbamic acid oxiranyl ethyl ester; and combinations thereof.

16. An epoxysilane selected from the group consisting of (3,4-bis-oxiranylmethoxycarbonylamino-phenyl)-carbamic acid 2-(dimethoxy-methyl-silanyl)-ethyl ester; [3-(diethoxy-methyl-silanyl)-propyl]-carbamic acid 3-oxiranylmethylcarbamoyloxy-2-oxiranylmethylcarbamoyloxymethyl-propyl ester; [3-(triethoxysilanyl)-propyl]-carbamic acid 2-oxiranylmethoxy-1-oxiranylmethoxymethyl-ethyl ester; (3-triethoxysilanyl-propyl)-carbamic acid 3-oxiranylmethoxy-2-oxiranylmethoxymethyl-2-(3-triethoxysilanyl-propylcarbamoyloxymethyl)-propyl ester; and (2-{2-[2-(2-oxiranylmethoxycarbonylamino-ethoxy)-ethoxy]-3-[(3-triethoxysilanyl-propylcarbamoyl)-methoxy]-propoxy}-ethyl)-carbamic acid oxiranylmethyl ester; and combinations thereof.

17. A curable composition comprising at least one epoxysilane of claim 1 and at least one additional component selected from the group consisting of filler, adhesion promoting agent, aqueous solvent, organic solvent, wetting agent, surfactant, organic resin film former, other organosilane, sizing agent, thixotropic agent, antistatic agent, antioxidant, UV light stabilizer, moisture scavenger, metal oxide, catalyst and acidic pH modifier.

18. The curable composition of claim 17 wherein the filler is at least one particulate material selected from the group consisting of chemically inert inorganic filler surface-reactive inorganic filler, sorptive inorganic filler and sorptive organic polymeric filler.

19. The curable composition of claim 17 formulated as a coating, metal surface-treating agent, conversion coating, sol-gel, adhesive, rubber, glass fiber size, potting compound, or sealant.

20. The epoxysilane of claim 1 produced by the process which comprises reacting epoxy alcohol with isocyanatosilane.

21. The epoxysilane of claim 1 produced by the process which comprises reacting epoxy alcohol with polyisocyanate to provide epoxyisocyanate and reacting the epoxyisocyanate with secondary aminoalkoxysilane and/or mercaptoalkoxysilane to provide epoxysilane.

22. The epoxysilane of claim 21 wherein the polyisocyanate possesses isocyanate groups of different reactivity.

23. The epoxysilane of claim 22 wherein the polyisocyanate is at least one diisocyanate selected from the group consisting of TDI, IPDI and TMDI.

24. The epoxysilane of claim 1 produced by the process which comprises reacting polyisocyanate with aminoalkoxysilane and/or mercaptoalkoxysilane to provide isocyanatosilane and reacting the isocyanatosilane with epoxy alcohol to provide epoxysilane.

25. The epoxysilane of claim 24 wherein the polyisocyanate possesses isocyanate groups of different reactivity.

26. The epoxysilane of claim 25 wherein the polyisocyanate is at least one diisocyanate selected from the group consisting of TDI, IPDI and MIDI.

27. The epoxysilane of claim 1 produced by the process which comprises reacting epoxy alcohol with ethylenically unsaturated isocyanate to provide ethylenically unsaturated epoxide and reacting the ethylenically unsaturated epoxide with hydridoalkylalkoysilane to provide epoxysilane.

28. The epoxysilane of claim 1 produced by the process which comprises reacting halocarbylsilane with cyanate in the presence of ethylenically unsaturated alcohol to provide ethylenically unsaturated alkoxysilane and expoxidizing the ethylenically unsaturated alkoxysilane to provide epoxysilane.

29. The epoxysilane of claim 1 produced by the process which comprises reacting halocarbylsilane with cyanate in the presence of ethylenically unsaturated alcohol to provide ethylenically unsaturated alkoxysilane and epoxidizing the ethylenically unsaturated alkoxysilane to provide epoxysilane.

30. A process for producing the epoxysilane of claim 1 which comprises reacting epoxy alcohol with isocyanatosilane.

31. The process for producing the epoxysilane of claim 1 which comprises reacting epoxy alcohol with polyisocyanate to provide epoxyisocyanate and reacting the epoxyisocyanate with secondary aminoalkoxysilane and/or mercaptoalkoxysilane to provide epoxysilane.

32. The process of claim 31 wherein the polyisocyanate possesses isocyanate groups of different reactivity.

33. The process of claim 32 wherein the polyisocyanate is at least one diisocyanate selected from the group consisting of TDI, IPDI and TMDI.

34. The process for producing the epoxysilane of claim 1 which comprises reacting polyisocyanate with aminoalkoxysilane and/or mercaptoalkoxysilane to provide isocyanatosilane and reacting the isocyanatosilane with epoxy alcohol to provide epoxysilane.

35. The process of claim 34 wherein the polyisocyanate possesses isocyanate groups of different reactivity.

36. The process of claim 35 wherein the polyisocyanate is at least one diisocyanate selected from the group consisting of TDI, IPDI and TMDI.

37. A process for producing the epoxysilane of claim 1 which comprises reacting epoxy alcohol with ethylenically unsaturated isocyanate to provide ethylenically unsaturated epoxide and reacting the ethylenically unsaturated epoxide with hydridoalkylalkoxysilane to provide epoxysilane.

38. A process for producing the epoxysilane of claim 1 which comprises reacting halocarbylsilane with cyanate in the presence of ethylenically unsaturated alcohol to provide ethylenically unsaturated alkoxysilane and epoxidizing the ethylenically unsaturated alkoxysilane to provide epoxysilane.

* * * * *